United States Patent [19]

Pituch

[11] Patent Number: 5,242,426
[45] Date of Patent: * Sep. 7, 1993

[54] MEDICAL NEEDLE SHEATH HOLDING APPARATUS

[76] Inventor: Daniel W. Pituch, 3299 Kennett Sq., Pittsburgh, Pa. 15213

[*] Notice: The portion of the term of this patent subsequent to Jun. 18, 2008 has been disclaimed.

[21] Appl. No.: 668,610

[22] Filed: Mar. 13, 1991

Related U.S. Application Data

[63] Continuation-in-part of Ser. No. 408,992, Sep. 18, 1989, Pat. No. 5,024,666.

[51] Int. Cl.⁵ ............................................. A61M 5/32
[52] U.S. Cl. ................................ 604/263; 604/192; 206/365; 29/281.1
[58] Field of Search ............ 604/110, 192, 263; 29/240, 281.1; 206/365-367; 269/24, 156, 265

[56] References Cited

U.S. PATENT DOCUMENTS

| | | | |
|---|---|---|---|
| 4,596,562 | 6/1986 | Vernon | 604/192 |
| 4,717,386 | 1/1988 | Simmons | 604/192 |
| 4,738,362 | 4/1988 | Burns et al. | 206/366 |
| 4,742,910 | 5/1988 | Staebler | 206/365 |
| 4,798,587 | 1/1989 | Willoughby | 604/110 |
| 4,862,573 | 9/1989 | Kelson | 206/366 |
| 4,867,309 | 9/1989 | Germain | 206/366 |
| 4,915,698 | 10/1990 | Levenson | 604/192 |
| 4,955,865 | 9/1990 | Steiner et al. | 604/192 |
| 4,989,307 | 2/1991 | Sharpe et al. | 206/366 |
| 5,013,299 | 5/1991 | Clark | 604/192 |
| 5,024,666 | 6/1991 | Pituch | 604/263 |
| 5,067,949 | 11/1991 | Freundlich et al. | 604/263 |
| 5,069,667 | 12/1991 | Freundlich et al. | 206/366 |
| 5,078,696 | 1/1992 | Nedbaluk | 604/263 |
| 5,143,414 | 9/1992 | Rosellini | 604/263 |
| 5,160,324 | 11/1992 | Halbach | 604/263 |

FOREIGN PATENT DOCUMENTS

| | | | |
|---|---|---|---|
| 296406 | 12/1988 | European Pat. Off. | 604/110 |
| 2199497 | 7/1988 | United Kingdom | 604/192 |
| 2205043 | 11/1988 | United Kingdom | 604/192 |
| 2215215 | 9/1989 | United Kingdom | 604/110 |

*Primary Examiner*—Ralph Lewis
*Attorney, Agent, or Firm*—Reed Smith Shaw & McClay

[57] ABSTRACT

Apparatus for permitting an individual to unsheath and resheath the needles of hypodermic syringes, catheters, etc., with the use of only one hand. The apparatus permits free use of the individual's other hand when such is required, e.g., when restraint of the patient is necessary in order to properly and safely administer an injection from a hypodermic needle or the like. The apparatus securely holds and positions a medical needle sheath during such times that a medical needle is removed from and reinserted into the sheath.

22 Claims, 14 Drawing Sheets

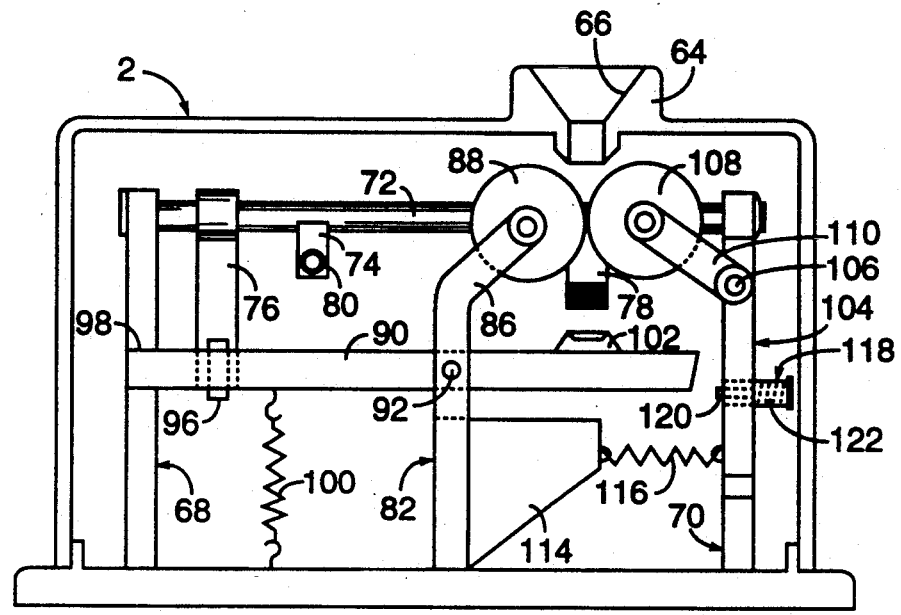
FIG. 14
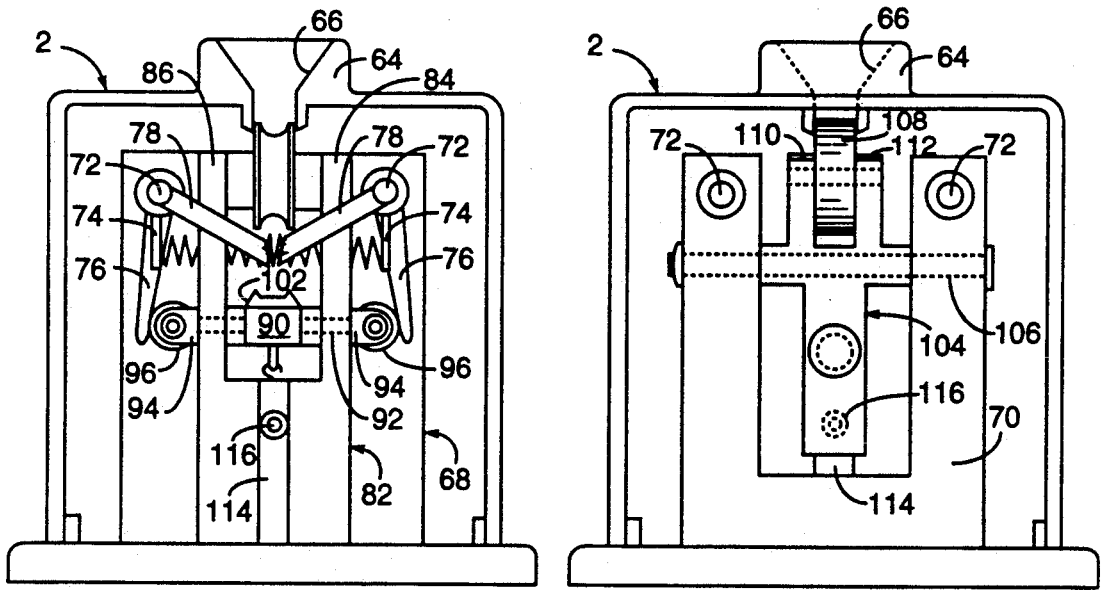
FIG. 15
FIG. 16

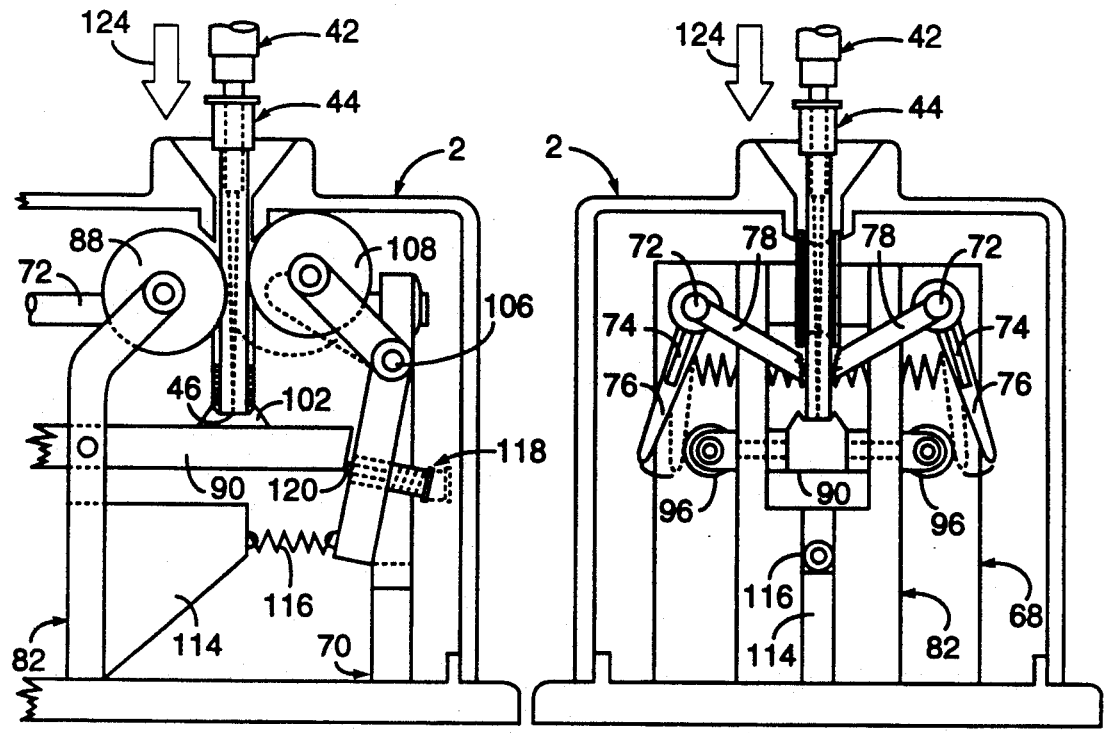
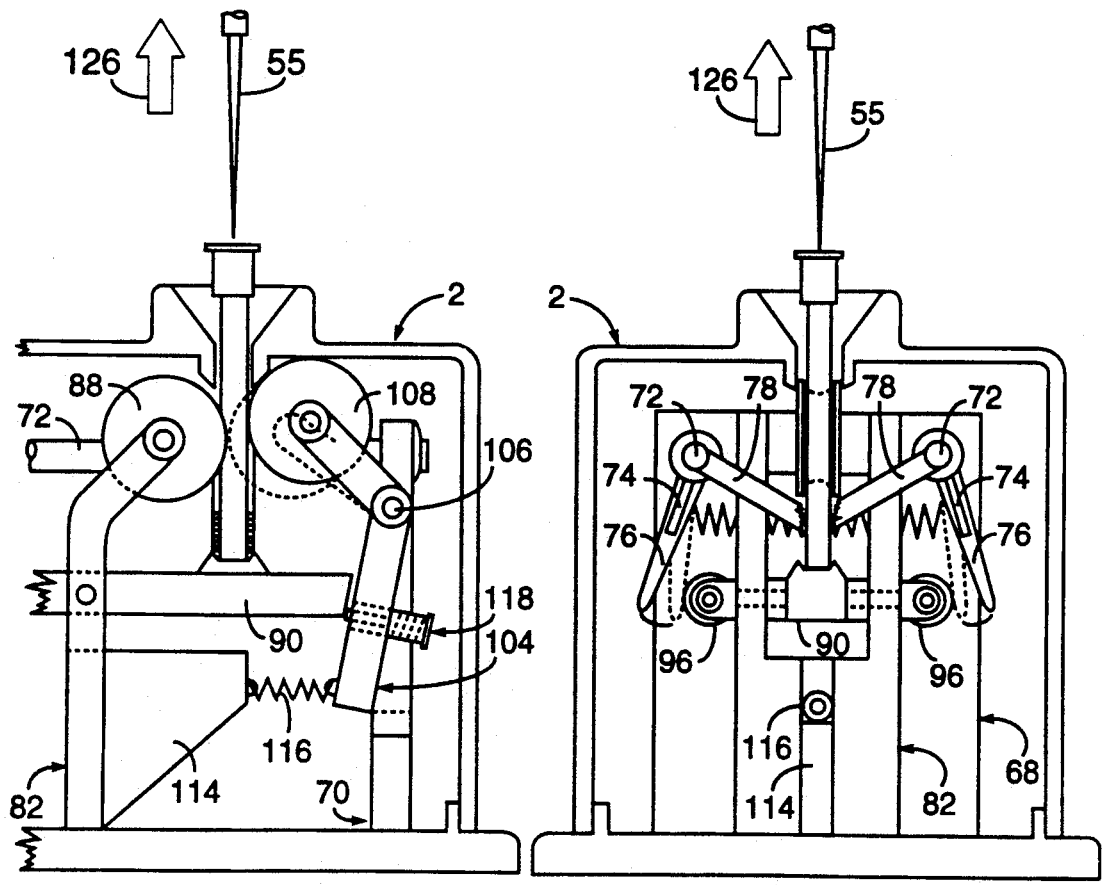
FIG. 17 FIG. 17a
FIG. 18 FIG. 18a

MEDICAL NEEDLE SHEATH HOLDING APPARATUS

This application is a continuation-in-part of U.S. patent application Ser. No. 07/408,992, filed Sep. 18, 1989, now U.S. Pat. No. 5,024,666.

BACKGROUND OF THE INVENTION

1. Field of the Invention:

The present invention generally relates to medical equipment, and more particularly to apparatus for securely holding the sheath or protective cap of a hypodermic syringe needle, catheter needle, or the like, during removal of the needle from the sheath and replacement of the needle into the sheath. Even more particularly, the present invention relates to a device which permits an operator to unsheath and resheath a medical needle with the use of only one hand.

2. Description of the Prior Art:

In the past, a number of devices have been introduced for the handling of hypodermic syringe needles, catheter needles, or the like, for the purposes of safety and/or prevention of the spread of disease.

The simplest class of such devices is represented in several forms in U.S. Pat. No. 4,742,910 to Staebler, U.S. Pat. No. 4,717,386 to Simmons and U.S. Pat. No. 4,596,652 to Vernon. Each of these documents describe, in various degrees of complexity, hand-held medical needle sheath removal and holder devices which require an operator to grasp the device in one hand and then, with the other hand, insert the sheathed needle into the device so that the device may remove and hold the sheath. After use of the syringe, or the like, the operator reinserts the needle into the sheath which is held in the holder device. In order to then remove the sheathed needle from the holder device, the operator must again grasp the holder device with one hand and then grasp and pull the sheathed needle portion of the syringe, or the like, from the holder with the other hand. Such devices, if used properly, will usually prevent accidental pricking by the medical needle and the spread of disease associated therewith.

A serious drawback with such devices, however, is that they require two hands in order to properly sheath and unsheath the needle. As can be appreciated, a doctor, nurse, or other medical technician does not always have the luxury of the free use of both hands at such times when a patient must be restrained, such as, for example, when a patient is violently writhing from pain, convulsions, madness, etc. During such instances, it is quite commonly required of the person performing an injection to use one of his or her hands to restrain at least the arm of the patient. Clearly then, during such moments of medical emergency, the person performing the injection cannot exercise the care required to properly operate the aforesaid sheath removal and holder devices. And with such disregard of the proper use or even the complete avoidance of the use of such equipment during these emergencies, the risk of accidental pricking with the needle and the potential spread of disease associated therewith increase dramatically.

Another disadvantage of such prior art devices is that they are unwieldy and impractical at such times when a surgeon, dentist, or the like, performs local anesthetic administration. For example, when the dentist or surgeon is palpating for landmarks, i.e., reference sites such as bones, tissue nodes, bumps or the like, which are used for precise positioning of the location of the injection, it is essential, especially if the landmarks are difficult to locate, that he maintain his fingers at the desired landmark or landmarks once they have been located. In this way the surgeon or dentist uses the positioning of his fingers as a guide for accurately placing the needle for injection.

However, with the prior art devices, the operator must use both hands to remove the sheath from the needle, thus requiring the operator to remove his fingers from the landmark if the landmark has already been located. If, however, the surgeon or dentist decides to first remove the sheath before palpating for landmarks, he thus leaves the needle exposed for an unduly prolonged length of time which again raises the likelihood of accidental pricking with the needle, particularly if the operator holds the syringe with one hand and palpates with the other.

Another shortcoming of the prior art needle sheath holders is that they are burdensome and may inhibit the rapid sequential administration of a number of injections of various types and quantities of drugs as is commonly performed by an anesthesiologist during a surgical operation. For example, prior to a surgical operation in which a patient is to receive general anesthesia, it is common for an anesthesiologist to prepare a number of syringes containing various concentrations and types of drugs, usually narcotics, for sequential injection into the patient through the use of a catheter. During such a procedure, it is not uncommon for various quantities of drugs from several of the syringes to be administered in relatively rapid sequence. It is also not uncommon for the anesthesiologist to use one or more of the syringes a number of times during the surgical procedure. For purposes of safety, i.e., in order to prevent accidental injection of an anesthetic into either the anesthesiologist or the other members of the surgical team, the needles of the syringes are preferably capped between usages and after their final usages. Bearing this in mind, one will appreciate that the anesthesiologist must spend a significant quantity of time and care in the unsheathing and resheathing of syringes during a surgical operation. If the surgery should become lengthy, the anesthesiologist may become fatigued and possibly neglect recapping of one more of the syringes between usages and after final usage. Along similar lines, if quantities of drugs from several of the syringes must be injected in rapid sequence, the anesthesiologist may neglect capping one syringe before using the next syringe. In either case, one or more of the needles may be left uncapped during the surgical procedure thus increasing the risk of accidental pricking of the medical personnel by the exposed needles.

A further problem exists in such a procedure. As noted previously, surgical operations may sometimes become quite lengthy and anesthesiologist may accordingly become fatigued. It is particularly at such times when the anesthesiologist is most likely to prick the hand which holds the needle sheath even if the sheath is retained in a sheath holder. To avoid these potential problems, the anesthesiologist must somehow be able to quickly, easily and assuredly unsheath and resheath the syringe needles at a first remote, yet easily reachable location, using only one hand, while keeping the other hand a safe distance therefrom. However, such a procedure is not possible using the sheath holder devices disclosed in the aforementioned U.S. Pat. Nos.

4,742,910, U.S. Pat. No. 4,717,386 and U.S. Pat. No. 4,596,652.

A somewhat more advanced form of medical needle sheath remover and holder device is disclosed in European Patent No. EP 0 296 406 A1. Described therein is a device which permits an individual to: 1) remove sheaths from medical needles, or 2) remove sheathed needles from a syringe, or the like, with the use of only one hand. While this device may represent an improvement over the previously mentioned prior art as far as removing the sheaths is concerned, it fails to provide any means for permitting resheathing of a needle after an injection is complete. If one using such a device desired to resheath the needle, one would first have to physically remove the sheath from the device and then replace the sheath onto the needle by hand, thus again requiring a "two-hand" operation to resheath the needle. Hence, such a device could not be effectively used by an anesthesiologist to uncap and recap needles in rapid succession. Furthermore, such a device would be of limited utility during some instances of medical emergency since, for reasons mentioned hereinabove, the medical personnel may not have the benefit of the free use of the "second hand" to resheath the needle during such times of emergency.

An advantage exists, therefore, for a device which will:

1) permit medical personnel to quickly and positively unsheath and resheath the needles of hypodermic syringes, catheters, etc., using only one hand, and 2) reduce the likelihood of accidental pricking with the needle by allowing an individual to maintain his hands at a safe distance from one another during unsheathing and resheathing of the needle, by permitting an individual to avoid premature unsheathing of the needle, and by permitting an individual to avoid unnecessarily prolonged periods of time in which the needle remains unsheathed.

It is therefore an object of the present invention to provide a device for permitting a person to quickly and positively unsheath and resheath the needles of hypodermic syringes, catheters, etc., using only one hand thus permitting unrestricted and free use of the person's other hand before, during, and after an injection into a patient is performed.

It is a further object of the invention to provide a device which reduces the likelihood of accidental pricking by the needle by permitting an operator to avoid both premature unsheathing of the needle and unnecessarily prolonged periods of time in which the needle is unsheathed.

It is a further object of the present invention to provide a device which permits a person to unsheath and resheath a medical needle while keeping his hands a safe distance from one another during the unsheathing and resheathing operation to thus reduce the likelihood of pricking of the person's hand not carrying the needle.

It is a further object of the invention to provide a device for securely holding and positioning a sheath during and after such time that a medical needle is removed therefrom as well as when the needle is reinserted thereinto.

It is a further object of the present invention to provide a device which will permit a series of needles to be unsheathed and resheathed in rapid succession.

It is a further object of the present invention to provide a medical needle sheath holder apparatus which is of a rugged, yet uncomplicated and inexpensive construction.

Still other objects and advantages will become apparent when one considers the attached drawings and written description of the invention provided hereinbelow.

SUMMARY OF THE INVENTION

In accordance with the present invention there is provided an apparatus for permitting an individual to quickly and safely unsheath and resheath the needles of hypodermic syringes, catheters, etc., with the use of only one hand. Consequently, the present invention permits free use of the individuals's other hand when such is required, e.g., when restraint of the patient is necessary in order to properly and safely administer an injection from a hypodermic needle, catheter, or the like.

According to a first preferred embodiment, the apparatus of the present invention comprises a housing having a reciprocable, spring biased base member provided therein. An actuator of a microswitch is in contact with a first side of the base member. Alternate depressions of the microswitch actuator by translation of the base member against the spring bias causes the microswitch to activate and deactivate a solenoid associated therewith. The solenoid and a needle sheath gripping means are carried on a second side of the base member so as to be translatable therewith. The needle sheath gripping means preferably includes a plurality of parallel plate-like members each having a bore therethrough.

In a first position of the solenoid, which carries one of the plate-like members on an arm thereof, the bores of the plate-like members are in alignment to permit a sheathed needle to be inserted thereinto or removed therefrom. In a second position of the solenoid, the bore of the plate-like member which is carried on the arm of the solenoid is misaligned relative to the bores of the other plate-like members so that the misaligned bores gently yet firmly grip the needle sheath received therein. In this position, a needle can be removed from or received in the sheath while the sheath remains retained in the grip of the misaligned bores.

The aforesaid depressions of the microswitch actuator which cause the microswitch to activate and deactivate the solenoid are effected by the exertion of manual force against the second side of the base member. Normally this exerted force is transmitted through the tip of the needle sheath which engages a striker plate fixed to the second side of the base member. The force thus directed against the base member by the sheath tip translates the base member against the force of the spring bias. Alternate translations of the base member against the spring bias cause the microswitch to operate the solenoid to alternatively misalign and align the bores of the gripping means so as to respectively grip and release a needle sheath positioned therein.

The apparatus may be portable or stationary and operated by either an AC or DC power supply. Preferably, a stop member is mounted to the housing to reduce premature wear and failure of the microswitch.

In further preferred embodiments of the invention, no AC or DC powered electromechanical means or other powered means, i.e., a solenoid, a pneumatic cylinder, or the like, is required to position the needle sheath gripping means between the gripping and non-gripping positions. Additionally in accordance with the further embodiments, the needle sheath gripping means comprise entirely mechanical mechanisms including an assembly of interconnected and interdependent members for gripping and releasing the needle sheath in response to alternate insertions of the medical needle into the needle sheath gripping means.

BRIEF DESCRIPTION OF THE DRAWINGS

FIG. 14 is a view taken along line XIV—XIV of FIG. 13;

FIG. 15 is a view taken along line XV—XV of FIG. 13;

FIG. 16 is a view taken along line XVI—XVI of FIG. 13;

FIGS. 17, 17A, 18, 18A, 19, 19A, 20, 20A, 21 and 21A illustrate a typical sequential operation of the second embodiment of the medical needle sheath holding apparatus of the present invention;

DESCRIPTION OF THE PREFERRED EMBODIMENTS

Figure 1:
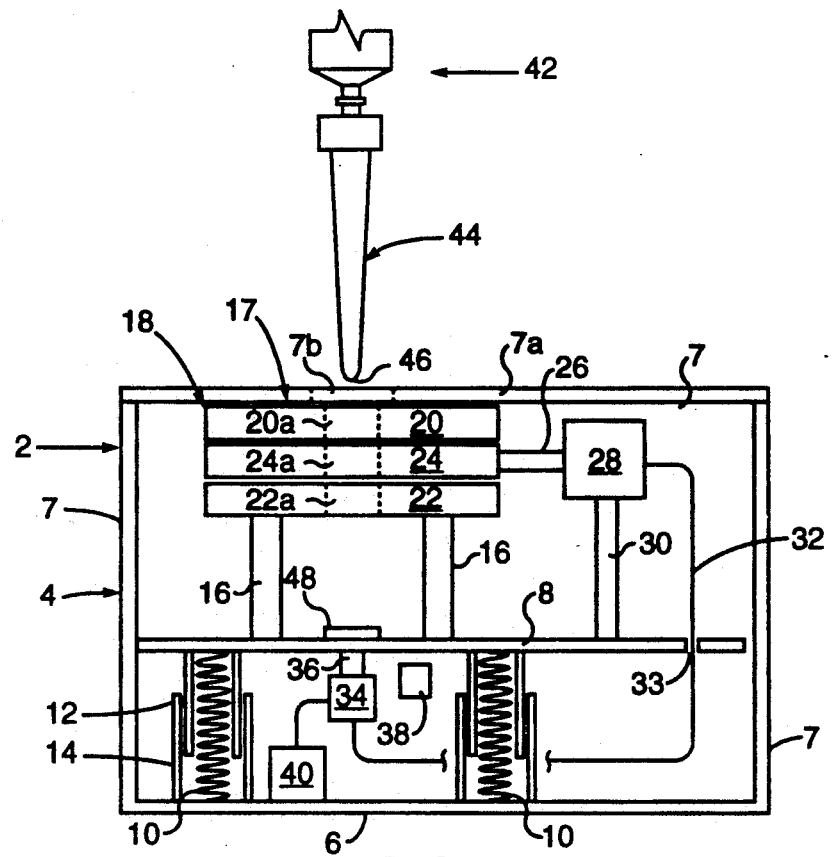
FIG. 1 is a side view of a first embodiment of the medical needle sheath holding apparatus of the present invention with a sidewall and other elements thereof omitted for purposes of clarity.

Referring now to FIG. 1 there is depicted a side view of a medical needle sheath holding apparatus 2 constructed in accordance with a first preferred embodiment of the present invention.

Sheath holding apparatus 2 normally includes a housing 4, a preferred embodiment of which will be described hereinafter, having a bottom portion 6, upstanding walls 7 (only three of which are shown in FIG. 1) and a top 7a. Reciprocably and guidingly supported within housing 4 is a base member 8. Fixed at first ends thereof to an inner or bottom side of base member 8 are a plurality of compression springs 10. At their opposite ends springs 10 are fixed to bottom portion 6 of housing 4. Each of the springs 10 is prevented from buckling and is guided during compression by virtue of its containment within tubular members 12 and 14. As will be appreciated from reference to FIGS. 1, 2, 4–6, and 8, top 7a acts as a stop for limiting upward translation of base member 8, and structure attached thereto to be described later, due to the bias of springs 10. Tubular member 12 is fixed to an inner or bottom side of base member 8 and is telescopically received in tubular member 14, itself being fixed to bottom portion 6.

Attached by support means 16 to an upper or outer surface of base member 8 is a stationary portion 17 or gripping means 18. Gripping means 18, in the first preferred illustrated embodiment, includes at least three substantially parallel plate-like members 20, 22 and 24. Plate-like member 20, as can be seen in FIG. 1, normally gently contacts the undersurface of top 7a due to the bias of springs 10. It is conceivable that two such plate-like members may be used to perform the sheath-gripping operation of apparatus 2, but for reasons to be described in greater detail hereinbelow, such a design is not preferred.

Figure 9:
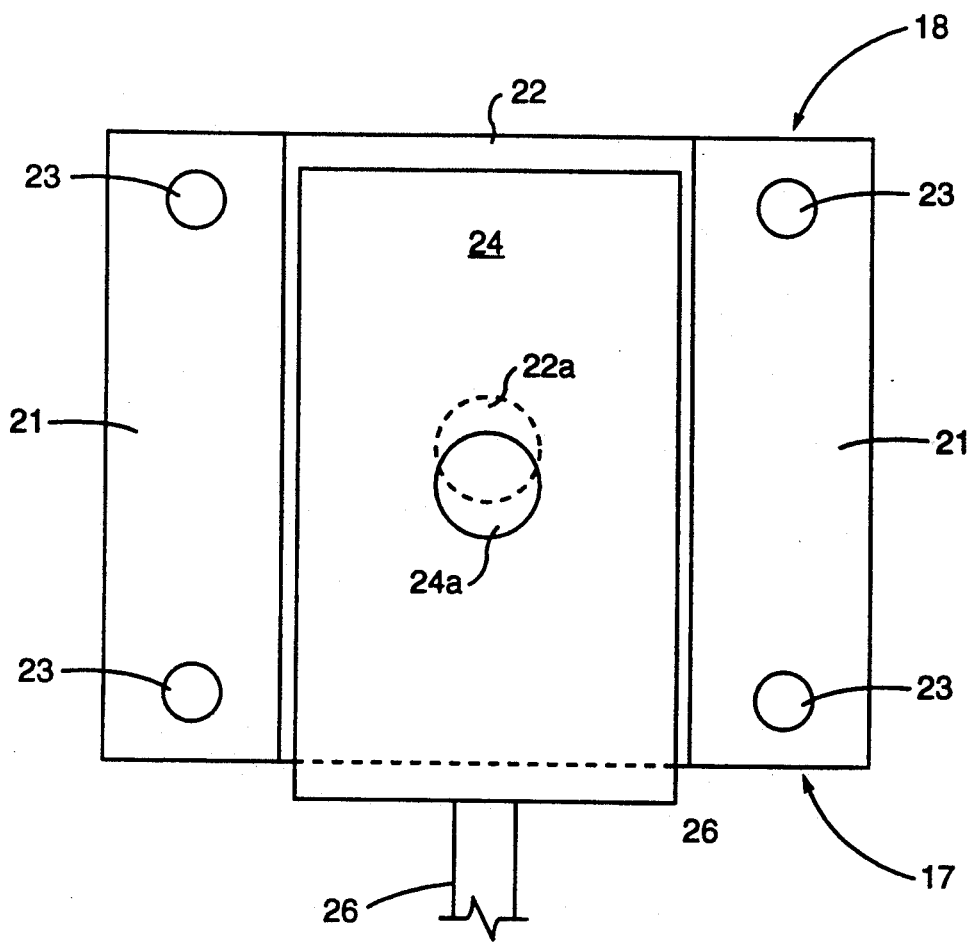
FIG. 9 is a plan view, with some elements omitted for purposes of clarity, of a first preferred needle sheath gripping means structure constructed in accordance with the present invention.
Figure 10:
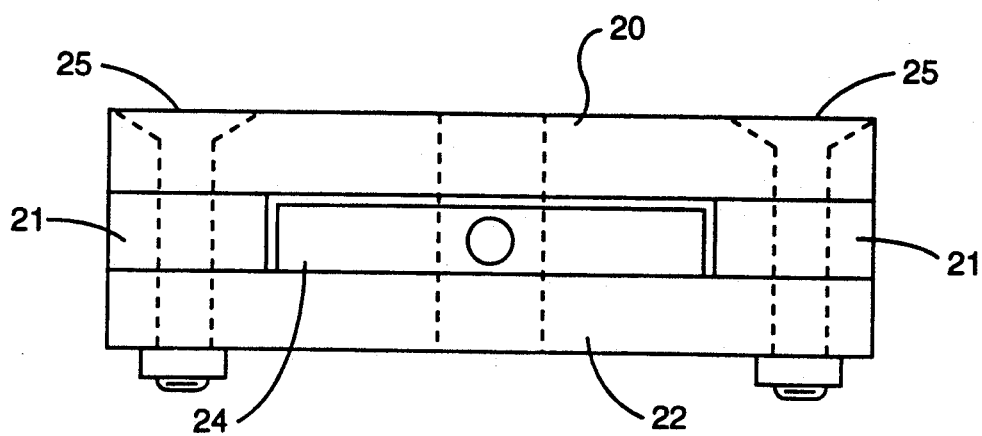
FIG. 10 is an end view of the needle sheath gripping structure illustrated in FIG. 9.

As can be seen in the drawing figures, with particular reference to FIGS. 9 and 10, plate-like members 20 and 22, which constitute the majority of the stationary portion 17 of gripping means 18, are preferably formed from separate parallel members arranged in such a manner that they are both fixed to and translatable with reciprocable base member 8 as well as being fixed in relation to one another. Plate-like member 24, which forms the movable portion of gripping means 18, is positioned between plate-like member 20 and 22. FIG. 9 illustrates the gripping means 18 in a "gripping" position which is described in greater detail hereinbelow.

As can be most clearly seen in FIG. 10, upper plate-like member 20 is spaced from lower plate-like member 22 by a pair of lateral spacer bars 21 which also form part of the stationary portion 17. Spacer bars 21 serve as lateral guides for plate-like member 24 as it reciprocates relative to the stationary portion 17, the operation of which is described hereinbelow. Plate-like members 20, 22 and spacer bars 21 are each provided with a plurality of holes 23 which are alignable with one another to receive a plurality of preferably removable fasteners 25, such as screws or bolts, for rigidly fastening plate-like members 20, 22 to one another and also to spacer bars 21. With such a construction plate-like member 24 is constrained by the inner surfaces of plate-like members 20, 22 and the inner surfaces of spacer bars 21 to reciprocate in a smooth linear fashion. Moreover, for smooth operation, the outer surfaces of reciprocal plate-like member 24 and/or the inner surfaces of plate-like members 20, 22 and spacer bars 21 in contact therewith may be coated with a friction reducing coating such as teflon, or the like.

Circular bores 20a, 22a and 24a are provided in plate-like members 20, 22 and 24, respectively. These bores are of sufficient diameter to accommodate the largest conventional needle or catheter sheaths such that when in alignment, they permit any conventional sheathed needle or catheter to be inserted therein or removed therefrom in a convenient linear stroke-like motion. Also, since most medical needle sheaths are substantially square in cross-section, a person inserting a sheathed needle into the circular bores does not have to first orient the sheath with the shape of the bores before inserting the sheath therein.

It is also contemplated, however, that gripping means 18 may assume other suitable configurations, such as, for example, a releasable clamping mechanism involving one or more jaw members which are reciprocable, pivotable or otherwise movable between gripping and non-gripping positions.

Continuing with the description of the first preferred embodiment of the present invention, an arm 26 is attached at a first end thereof the plate-like member 24 and at a second end thereof to a reciprocable actuator such as solenoid 28. Solenoid 28 is fixedly secured to base member 8 via support 30 so as to be translatable with base member 8. An electrical line 32 connected to solenoid 28 passes through an aperture 33 provided in base member 8. For purposes of compactness, electrical line 32 may be extended through a passageway in support 30, if desired. At its opposite end electrical line 32 is connected to microswitch 34 which, in turn, is fixed to housing 4. An actuator 36 extending from microswitch 34 extends to, and preferably contacts, the inner or bottom side of base member 8.

Downward or inward translation of base member 8 is limited by contact of the inner side of the base member with stop member 38 which is preferably adjustably fixed to a wall 7 of housing 4. The purpose of stop member 38 is to limit excessive compression of microswitch actuator 36 to thereby prevent premature wear and failure of microswitch 34.

Power for operating for medical needle sheath holding apparatus 2 is provided by power source 40 which is connected to microswitch 34. It is contemplated that power source 40 may either be an AC or DC power source depending, inter alia, on the degree of portability required of the needle sheath holding apparatus 2.

Although not illustrated, it is contemplated that other suitable means, such as pneumatic or hydraulic pressure, vacuum, or the like, may be used for reciprocating plate-like member 24. For example, if pneumatic pressure is used, power source 40 in this instance would supply pressurized air from an external source which, in turn, would serve as a pressurized air source for a reciprocable pneumatic actuator connected to arm 26. Microswitch 34 would be replaced by a suitable two-position valve which would either supply pressurized air to or exhaust pressurized air from an air line communicating the compressed air with the reciprocable pneumatic actuator. The reciprocable actuator, like solenoid 28, would normally be biased to a position in which the bores 20a, 22a, and 24a are in alignment, i.e., a non-gripping position. As discussed above with regard to the actuation of microswitch 34, an actuator, similar to actuator 36, would be operably connected to the two-position valve such that alternate inward translations of the base member 8 would cause the two-position valve to perform the aforesaid supplying or exhausting of pressurized air to the pneumatic actuator. When supplied with pressurized air, the pneumatic actuator will move arm 26 and, hence, plate like member 24 to the gripping position; and when exhausted of pressurized air, the pneumatic actuator will move arm 26 to the non-gripping position.

The reader will appreciate that analogous arrangements may be created for hydraulic pressure systems, vacuum systems, or other possible alternative systems, in order to effectively translate plate-like member 24 relative to plate-like members 20 and 22 so as to urge the gripping means 18 either into or out of gripping position.

Continuing with the description of FIG. 1 there can be seen represented by element 42 a hypodermic syringe, catheter, or the like, the needle of which is covered by a sheath 44 which, as noted previously, is usually of a square outer cross-section. At the lower portion of sheath 44 is a tip 46 for contacting a striker plate 48 attached to the outer or upper side of base member 8 as will be described in greater detail hereinbelow.

Operation of the medical needle sheath holding apparatus to will now be discussed with reference to the sequential illustrations of FIG. 2 through FIG. 8.

Figure 2:
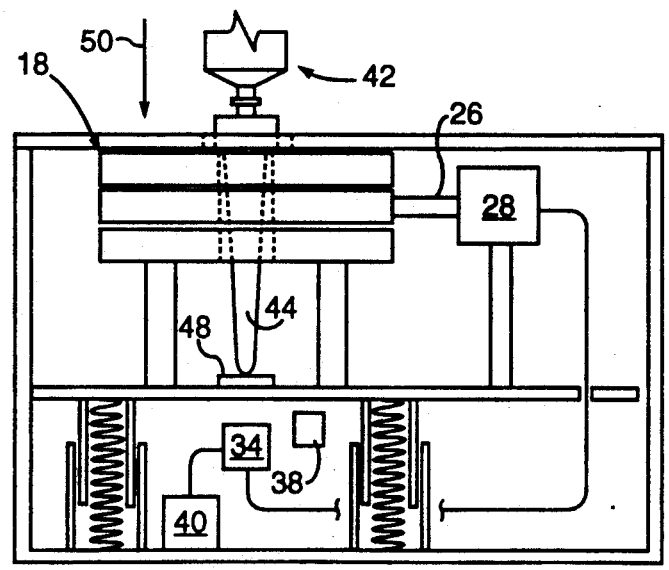
FIG. 2 through FIG. 8 illustrate along with FIG. 1, a typical sequential operation of the first embodiment of the medical needle sheath holding apparatus of the present invention.

As can be seen in FIG. 2, bores 20a, 22a and 24a of plate-like members 20, 22 and 24 are in alignment with one another as well as with a bore or opening 7b in top 7a which is of somewhat larger diameter than bores 20A and 22A. Such a condition, for purposes of discussion only, will hereinafter be referred to as representing a "deactivated" condition of solenoid 28 and gripping means 18. When bores 20a, 22a and 24a are aligned, the sheathed syringe or catheter 42 is then inserted in the direction of arrow 50 into the aligned bores until the tip 46 of the sheath 44 contacts the upper or outer surface of striker plate 48. Striker plate 48 is of sufficient height or is adjustable thereto, or, alternatively, support means 16 and support 30 may be of a preselected minimum height or adjustable thereto, such that the tip 46 of any conventional medical needle sheath inserted in the aligned bores will contact the striker plate 48, regardless of the length of the sheath.

Figure 3:
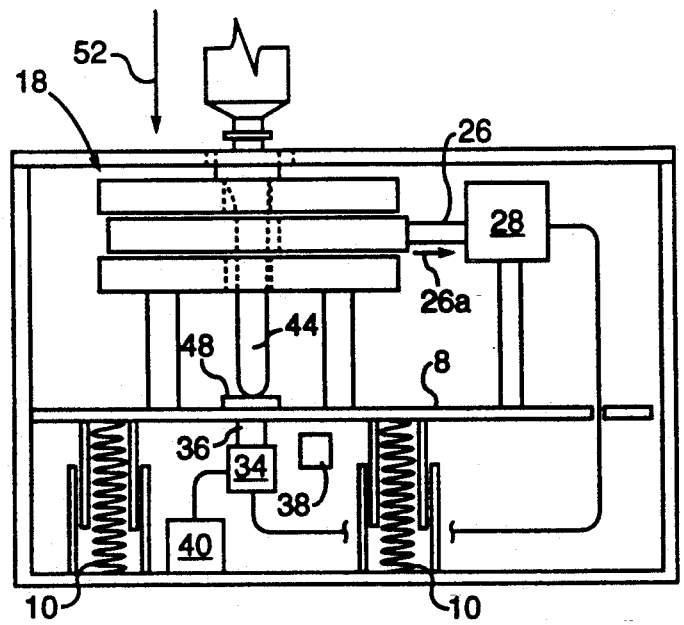

Proceeding to FIG. 3, it can be seen that continued force exerted by the catheter or syringe 42 in the direction of arrow 52 causes the tip 46 of the sheath to displace the gripping means 18 and, hence, base member 8 downwardly or inwardly against the bias of spring 10. Displacement of the base member 8 causes a corresponding displacement of the microswitch actuator 36 to the level of the outer surface of stop means 38 which, in turn, causes the microswitch 34 to activate the solenoid 28. Actuation of the solenoid 28 displaces the arm 26 and thereby movable plate-like member 24 of gripping means 18 in the direction of arrow 26a. In such a position the gripping means 18 is considered to be in an "activated" condition. It will be appreciated that the solenoid 28 may be activated to move the plate-like member 24 in a direction opposite to or substantially lateral to arrow 26a, if so desired, so long as the solenoid causes the bore 24a to become displaced relative to bores 20a and 22a in a manner similar to that depicted in FIG. 3. Moreover, the degree of displacement of bore 24a relative to bores 20a and 22a is preferably adjustable to gently yet firmly hold sheaths 44 of various sizes while avoiding bending or shearing of the needles encased within the sheaths. Moreover, as aforementioned, bores 20a, 22a and 24a are preferably circular in order to positively engage the usually square periphery of the sheath 44 and, at the same time, such circular bores eliminate any need for an operator to positively and deliberately align the outer cross-section of the sheath in the aligned bores before it is placed therein.

As mentioned hereinabove, it is contemplated that only two plate-like members rather than three may be used in the sheath holding apparatus, if desired. Such a situation is not preferred, however, since the movable plate-like member, when displaced, will tend to tilt the hypodermic needle or syringe 42 when it is received in the apparatus 2. Moreover, it is not believed that the provision of only two plate-like members will hold a sheath as securely as the three plate system disclosed herein at such times when the needle is to be inserted in or removed from the sheath.

Figure 4:
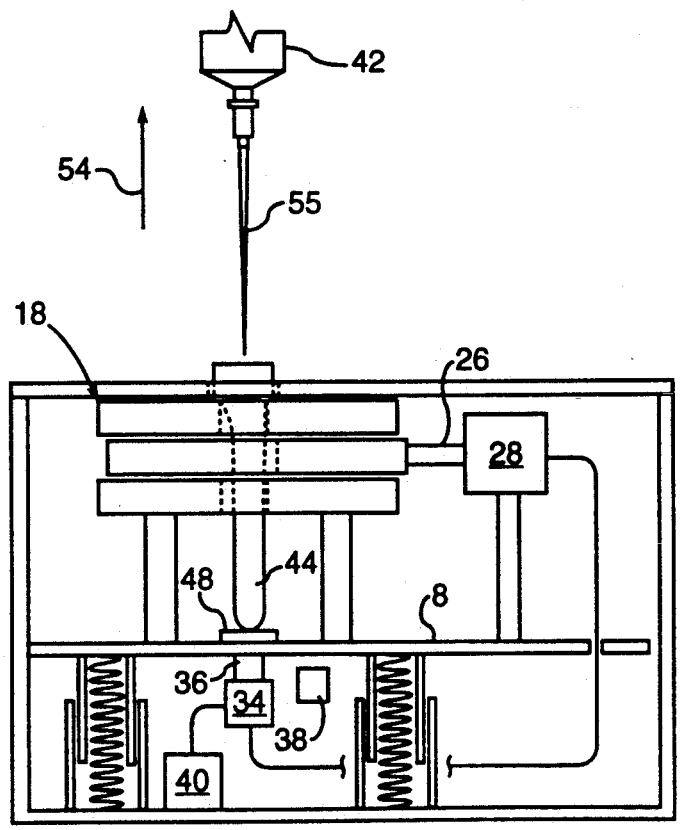

With reference now to FIG. 4, it can be seen that with the sheath 44 now firmly held in griping means 18, the syringe or catheter 42 and the needle 55 attached thereto can be removed from apparatus 2 by exerting a force on the syringe or catheter 42 in the direction indicated by arrow 54. This, in turn, permits the biasing force in springs 10 to return base member 8 to its initial level and the upper surface of plate-like member 20 into gentle contact with the undersurface of top 7a. At such time, microswitch actuator 36 also returns to its initial "extended" position.

FIGS. 1 through 4, therefore, graphically illustrate the unsheathing of a needle 55 of a hypodermic syringe, a catheter 42, or the like, using the novel needle sheath holder apparatus 2 of the present invention. FIGS. 5 through 8, to be described hereinbelow, depict the resheathing of needle 55.

Figure 5:
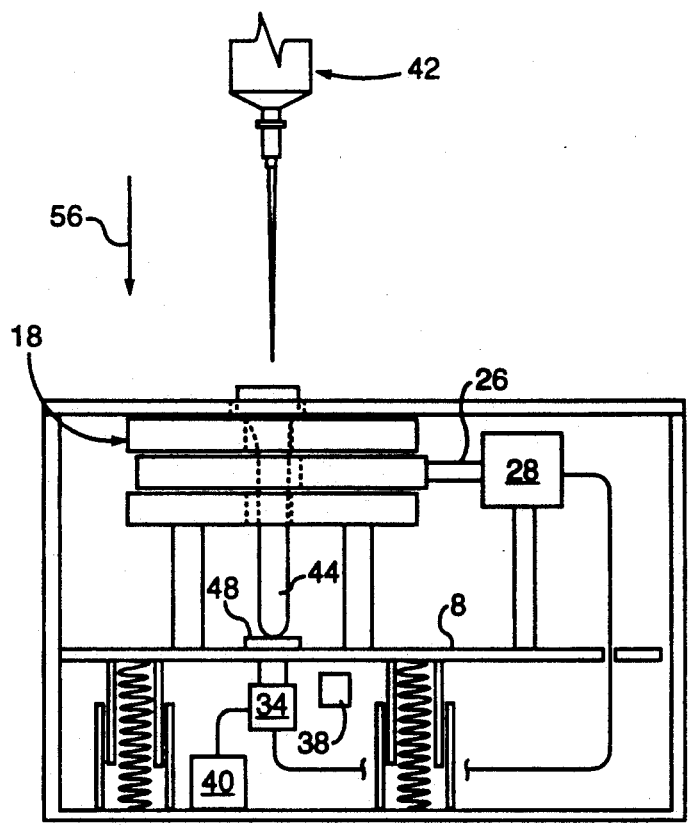
Figure 6:
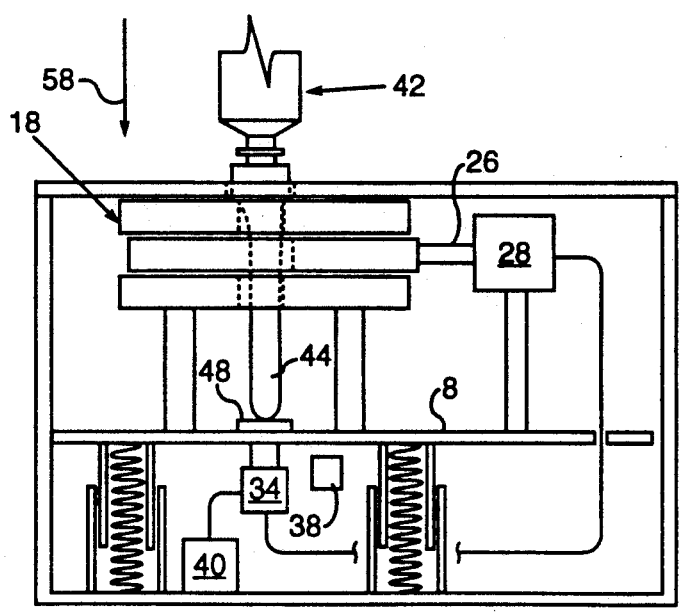
Figure 7:
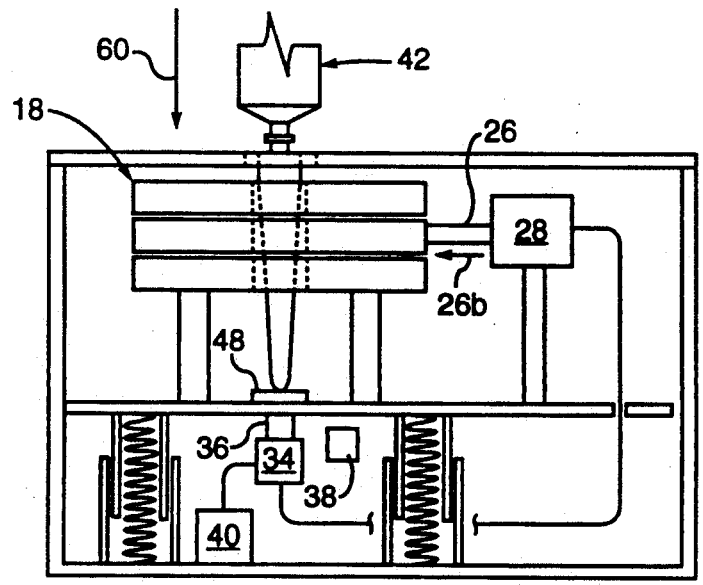
Figure 8:
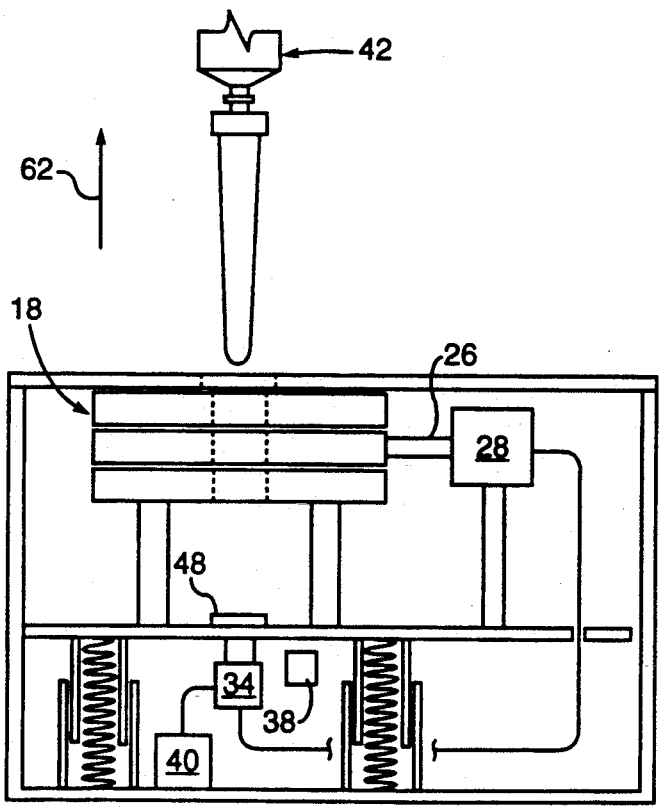

FIG. 5 is substantially identical to FIG. 4 except it will now be appreciated that the syringe or catheter 42 has been used and needle 55 is about to be resheathed. Accordingly, syringe or catheter 42 is inserted in the direction indicated by arrow 56 (FIG. 5) and arrow 58 (FIG. 6) into the sheath 44 which is retained in gripping means 18. Continued downward force exerted by the syringe or catheter 42 in the direction of arrow 60 (FIG. 7) once again displaces base member 8 against the force of biasing springs 10 until the base member contacts stop means 38. As before, the microswitch actuator 36 is correspondingly displaced to thereby cause the microswitch 34 to "deactivate" the solenoid 28. Deactivation of solenoid 28 moves plate-like member 24 in the direction indicated by arrow 26b to realign bores 20a, 22a and 24a as seen in FIG. 7. At this time, the resheathed needle 55 and its syringe or catheter 42 may be removed from apparatus 2 by pulling the catheter or syringe in the direction indicated by arrow 62 in FIG. 8. Accordingly, base member 8 reattains its initial level due to the bias of springs 10, and microswitch actuator 36 is similarly returned to its initial extended condition. The configuration of FIG. 8 is identical to FIG. 1 and the medical needle sheath holder apparatus 2 of the present invention is prepared to again unsheath a catheter or syringe needle.

Other suitable means, e.g., an appropriately positioned photoelectric call and light beam system, may be used in place of microswitch 34 for actuation of solenoid 28. In such an arrangement, insertion of a sheathed needle interrupts the light beam thus causing an associated two-position switch to assume a first position to activate solenoid 28 to move gripping means 18 into a sheath-gripping position. Following this, the needle can be unsheathed and removed from apparatus 2 in the manner described hereabove, whereby the light beam to the photoelectric cell is restored. Upon reinsertion of the needle into apparatus 2 and the gripped sheath, the light beam is again interrupted, whereupon the two-position switch assumes its second position to deactivate the solenoid 28 to move gripping means 18 into its non-gripping position such that the sheathed needle can be removed from the apparatus.

While not illustrated, it is contemplated that housing 4 may be fixed to any horizontal or inclined surface by suitable conventional hardware. Moreover, the apparatus 2 may be completely portable and battery-powered in which case it has particular advantageous application for field usage by emergency medical personnel such as paramedics.

The major components of the apparatus 2, i.e., housing 4, base member 8 and plate-like members 20,22 and 24 may be formed of durable plastic, metal, or the like.

Figure 11:
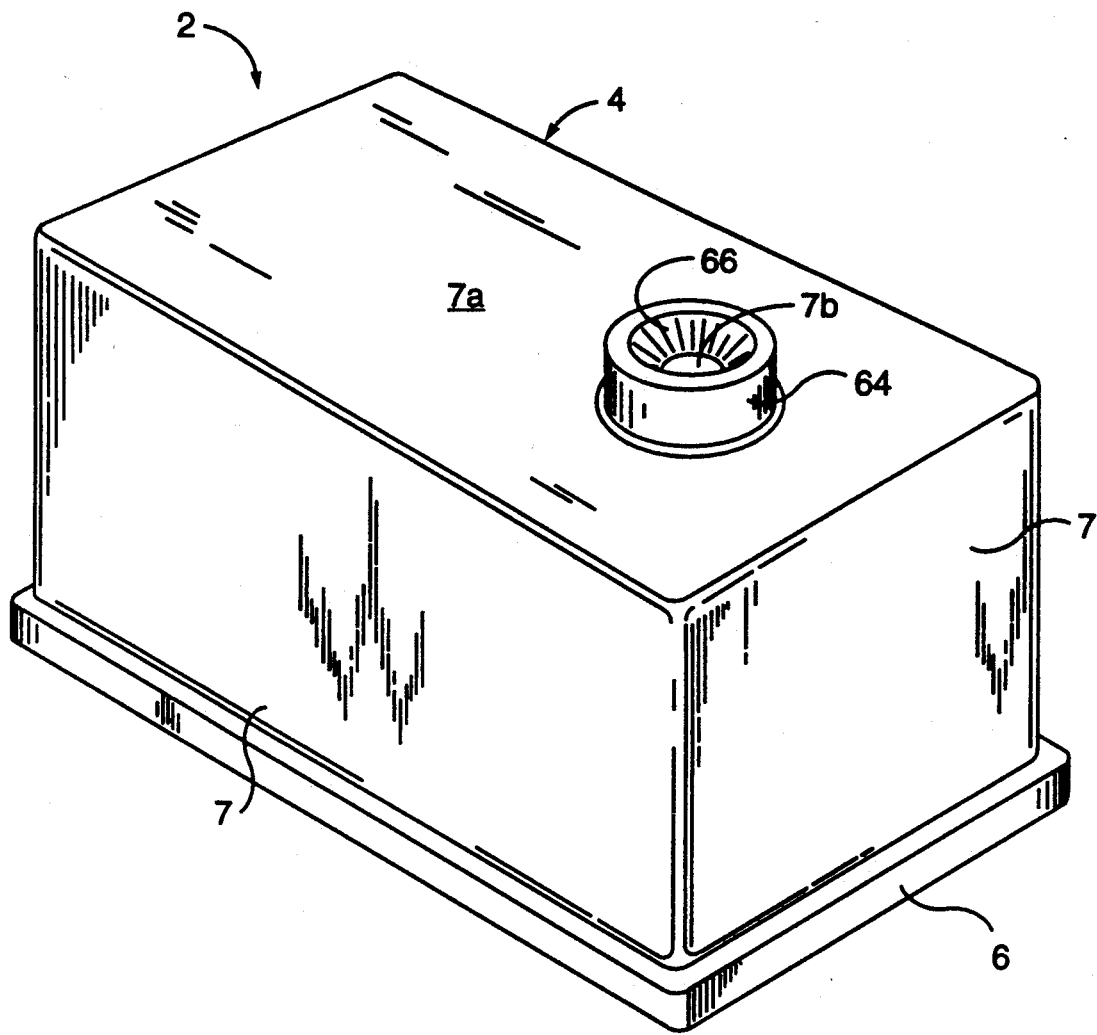
FIG. 11 is a perspective view of a housing suitable for use in permanent and semi-permanent versions of the medical needle sheath holding apparatus of the present invention.
Figure 12:
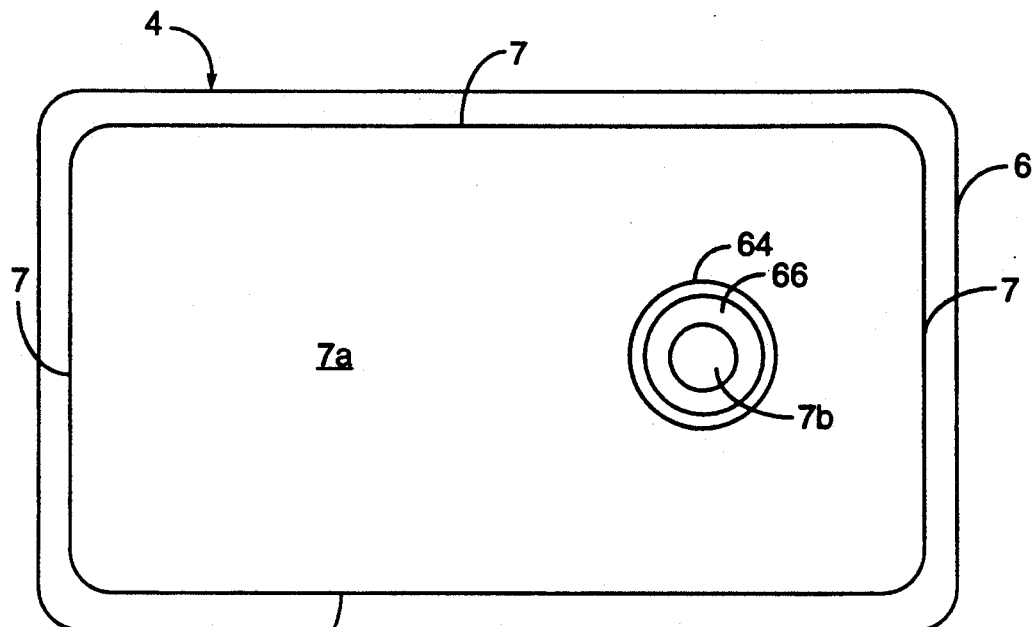
FIG. 12 is a plan view of the housing shown in FIG. 11.

FIGS. 11 and 12 show a preferred form of the housing 4 for use with a number of the semi-portable and fully portable versions of the apparatus 2 described herein. Although not shown in FIGS. 11 and 12, it will be understood that in semi-portable versions of the apparatus, housing 4 either will be provided with an integral power supply cord or will have appropriate fittings to connect the housing as required to sources including, inter alia, electrical power, pressurized air, or a source of vacuum.

Additionally, although not shown for purposes of clarity in previously described figures, it is preferred that opening 7b in top 7a of housing 4 be surrounded by a raised guide member 64 having a tapered inner wall 66 which serves to assist in guidance of the medical needle (sheathed or unsheathed) as it is inserted into the apparatus 7.

Turning to FIGS. 13 through 16, wherein like references indicate similar elements, as is true in the remaining views, there is shown the operational components a second preferred embodiment of the present invention. According to this embodiment the medical needle sheath holding apparatus 2 is unpowered. That is to say, it is wholly and entirely mechanical in operation and does not depend in any way upon electrical power, vacuum, hydraulic pressure, pneumatic pressure, or the like, for motive force or operating power. These figures reveal that a first upstanding support member 68 and a second upstanding support member 70 are affixed to the bottom portion or base 6 and freely rotatably support near the upper ends thereof opposite ends of a pair of spaced-apart, parallel shafts 72. Integrally fixed to each shaft 72 is a tab member 74, a force-transmitting runner member 76, and a jaw member 78, each of which is mounted on one of the pair of shafts 72 in direct opposition to its counterpart on the other of the pair of shafts. The opposed tab members 74 are connected and biased toward one another by elastomeric means under tension, preferably by a tension spring 80.

Affixed to the base 6 of housing 4 at a location intermediate the first and second upstanding support members 68 and 70 is a third upstanding support member 82, the upper portion of which defines a yoke in the form of spaced arms 84 and 86. The distal ends of arms 84 and 86 rotatably support, through suitable spacing means, a first frictionless pulley 88 having a substantially semicircular circumferential groove formed therein.

An elongated generally horizontally extending lever 90 is pivotally mounted at 92 to arms 84 and 86 below pulley 88.

Figure 13:
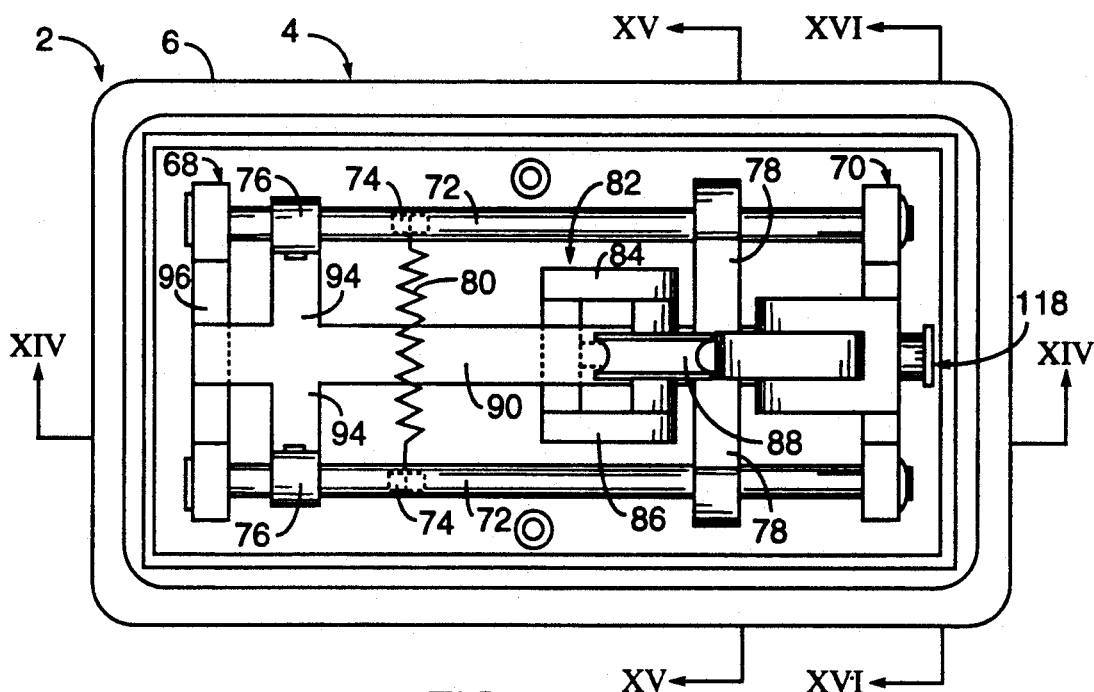
FIG. 13 is a plan view of a second embodiment of the medical needle sheath holding apparatus of the present invention with a housing top omitted for purposes of clarity.

As is perhaps most clearly shown in FIG. 13, lever 90 has a pair of laterally protruding runner displacement members 94 extending from opposite sides thereof.

Each of the runner displacement members 94 supports on its free end a frictionless caster wheel 96 which rolls along and displaces a respective runner member 76, in a manner which will be described hereinbelow, during operation of the second embodiment of the medical needle sheath holding apparatus 2 of the present invention. Due to the tension in spring 80 which draws tab members 74 toward one another, runner members are also biased to rotate toward one another by virtue of their integral connection with shafts 72. The inwardly directed forces thus exerted by the runner members 76 cause the caster wheels 96 supported by runner displacement members 94 to normally roll downwardly along the runner members until a first end of the lever 90 comes to rest on a stop surface 98 of the first upstanding support member 68. In such a condition, the apparatus 2 in accordance with the second embodiment of the present invention, is in a "ready" postion to receive a sheathed medical needle. To assure that the second preferred embodiment of apparatus 2 always returns to its "ready" position upon completion of a medical needle unsheathing and resheating operation, it is preferred that a resilient member such as, for example, tension spring 100 be connected to the lever 90 and the housing bottom portion or base 6 between upstanding support members 68 and 82, to exert downward restoring force on lever 90 in addition to that provided by tension spring 80.

Positioned atop the lever 90 near a second and thereof is a striker plate 102 that receives impact from a medical needle sheath in a manner similar to striker plate 48 which was described hereinabove with regard to the first preferred embodiment of the present invention.

A yoke member 104 is pivotally mounted at 106 to the second upstanding support member 70 as is most clearly illustrated in FIG. 16. A second frictionless pulley 108 is rotatably supported generally opposite to pulley 88 at an upper end of yoke member 104 between spaced arms 110 and 112. Pulley 108 is supported by arms 110 and 112 at an elevation and lateral position generally the same as that of pulley 88 whereby the pulleys 88 and 108 cooperate with one another during operation of the second preferred embodiment of the present invention. It is preferred that the second pulley 108 be provided with little or no circumferential groove (FIG. 13) in order that the medical needle sheath can be positively retained in and guided by the groove formed in pulley 88. If pulley 108 were provided a circumferential groove as deep or nearly as deep as that provided in pulley 88, it is possible that during operation of the second embodiment of the invention the medical needle sheath may slip between the pulleys without being removed from the hypodermic needle, catheter, or the like. As an alternative to that shown, it is conceivable that each of pulleys 88 and 108 can be provided with comparable relatively shallow circumferential grooves. However, such a construction is not preferred since it is believed that it would not normally provide the optimum combination of sheath guidance and engagement obtained by the illustrated pulley configurations. Moreover, the reader will appreciate that, if desired, pulley 88 can be essentially grooveless and pulley 108 provided with a relatively deep circumferential groove without changing the operation of the second embodiment of apparatus 2.

An abutment 114 is formed on a lower portion of the third (intermediate) upstanding support member 82 and extends in the direction of yoke member 104. A resilient compressible means 116, herein depicted as a compression spring, is connected at its opposite ends to abutment 114 and a lower portion of yoke member 104. The restoring force in spring 116 urges the yoke member 104 to pivot about pivot means 106 such that, in the aforementioned "ready" position, pulley 108 contacts pulley 88 in the manner shown in FIGS. 13 and 14.

A latch mechanism 118, the function of which will be described hereinbelow, is carried by yoke member 114. The latch mechanism 118 includes a latch member 120 which is normally biased by a compression spring 122, or the like, to project a predetermined distance from the lower portion of yoke member 114 in a direction toward the second end of the lever 90 as illustrated in FIG. 14. It is conceivable however that latch member 122 could simply be a fixed and unbiased protruding formation provided on the lower portion of yoke member 114.

A more complete appreciation of the operation of the second preferred embodiment of the present invention will be had upon the following discussion concerning FIGS. 17, 17A, 18, 18A, 19, 19A, 20, 20A, 21 and 21A. FIGS. 17, 18, 19, 20 and 21 represent partial side elevation views of the apparatus 2 (with some elements and details omitted for purposes of clarity). FIGS. 17A, 18A, 19A, 20A and 21A depict section views, in elevation, taken transversely through apparatus 2 substantially in a plane located just to the right of striker plate 102 and correspond to the same instances in time captured in FIGS. 17, 18, 19, 20 and 21 (again, with some elements and details omitted for purposes of clarity).

Turning first to FIGS. 17 and 17A, in order to begin a medical needle unsheathing and resheathing operation, a sheathed syringe or catheter 42 is inserted into the apparatus 2 between pulleys 88 and 108, whereby the sheath 44 displaces the pulley 108 from the "ready" position depicted in FIG. 14. The syringe or catheter 42 is inserted into the apparatus in the direction indicated by arrow 124 until the tip 46 of the sheath 44 contacts the striker plate 102. Insertion is then stopped. As the syringe or catheter 42 is inserted, the sheath 44 is guided by the circumferential groove in pulley 88 and at the same time causes displacement of pulley 108. The compression spring 116 is compressed during this period in time, hence it exerts a reaction force against the lower portion of yoke member 104 to maintain pulley 108 against one wall of the sheath 44 and the opposite wall of the sheath in the groove of pulley 88.

During insertion of the syringe or catheter 42 to the depth indicated in FIGS. 17 and 17A, the gripping surfaces of jaw members 78, like the pulleys 88 and 108, become separated from one another while grippingly engaging opposite sides of the wall of the sheath 44. The gripping surfaces of jaw members 78 remain in compressive gripping contact with the sheath by virtue of tension spring 80 which draws tab members 74 toward one another which in turn applies inwardly directed moments to shafts 72, thereby causing jaw members 78 to be forced inwardly toward one another. The gripping surfaces of the jaw members 78 are also preferably serrated, substantially as illustrated, in order to enhance their capacity to grip the sheath 44. Simultaneous with initial insertion of the syringe or catheter 42, the runner members 76 (FIG. 17A) are displaced from a "ready" position in contact with caster wheels 96, as indicated in phantom line, to a slightly angularly displaced position spaced from the caster wheels, as indicated in solid line, due to the physical separation of the gripping edges of the jaw members by the sheath 44.

With reference now to FIGS. 18 and 18A, it will be appreciated that with the sheath 44 now firmly held between jaw members 78, the syringe or catheter 42 and the needle 55 attached thereto can be removed from apparatus 2 by exerting a force on the syringe or catheter 42 in the direction indicated by arrow 126. While the syringe or catheter 42 is removed from the apparatus 2, the gripping means, i.e., jaw members 78, and the pulleys remain in contact with the sheath 44 as indicated in FIGS. 18 and 18A.

Figures 19, 19A:
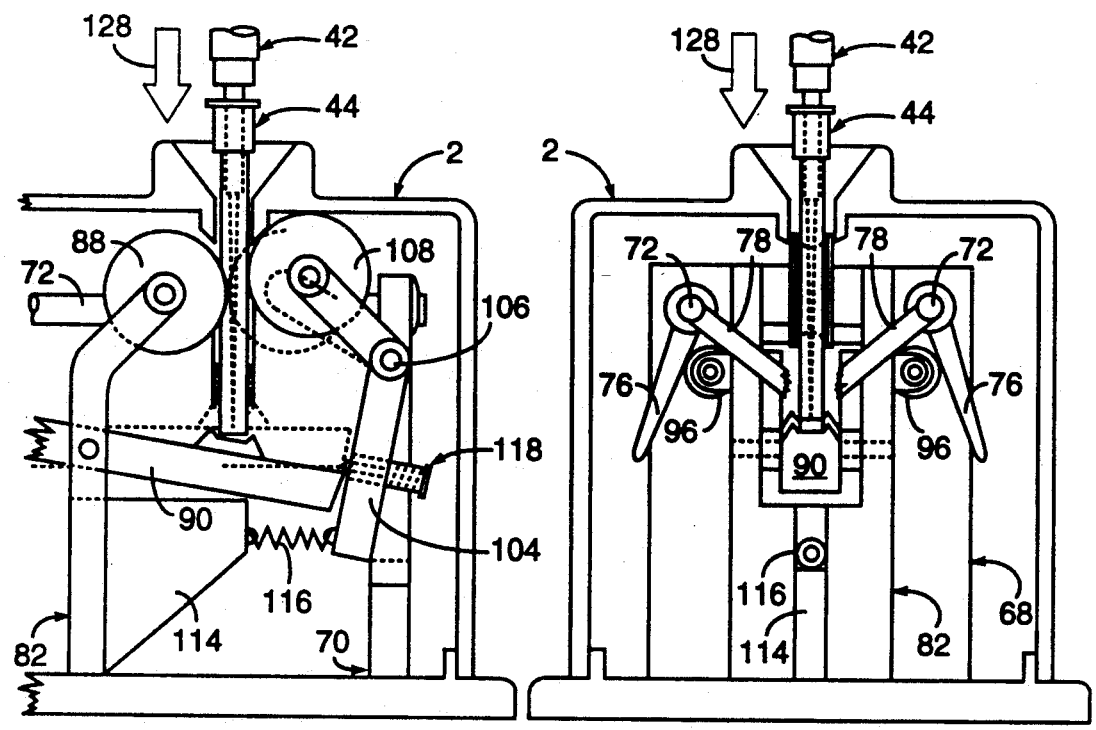

When it is desired to resheath the needle 55 of syringe or catheter 42, the needle is reinserted into sheath 44 as shown in FIGS. 19 and 19A and continued downward force is exerted in the direction at arrow 128. As this downward force is exerted, the second end of lever 90 is caused to pivot from the substantially horizontal position shown in phantom line in FIG. 19 to the latched position shown in solid line. During this transition, the end face at the second end of the lever 90 first inwardly displaces latch member 120 against the force of compression spring 122, which force is substantially less than that of spring 116, until the upper edge of the lever 90 passes the latch member 120 and the latch member is again forced outwardly due to the force in spring 122 to retain the second end of lever 90 in the latched condition. In order to assure that the sheath 44 is firmly snapped back onto the syringe or catheter 42, it is preferred that the operator continue exertion of force in the direction of arrow 128 until the operator detects resistance arising from contact of the lever 90 against the top of abutment 114.

Concurrent with the latching operation of the second end of the lever 90, the first end of the lever is pivoted upwardly. During this time, caster wheels 96 roll upwardly along force transmitting runner members 76 which in turn causes the runner members to angularly spread outwardly away from one another, thereby causing outward cranking of shafts 72 and jaw members 78. When lever 90 is fully latched, caster wheels 96, runner members 76 and jaw members 78 assume the positions shown in FIG. 19A. In such condition, the jaw members 78 are displaced from and retained against gripping contact with the wall of sheath 44. If desired, runners 76 may be slightly curved to accomodate the slight arc traversed by caster wheels 96 as they are transported between their "ready" and "latched" positions.

Removal of the resheathed syringe or catheter 42 and return of the second preferred embodiment of apparatus 2 to its ready position will be appreciated with reference to FIGS. 20, 20A, 21 and 21A.

Figures 20, 20A:
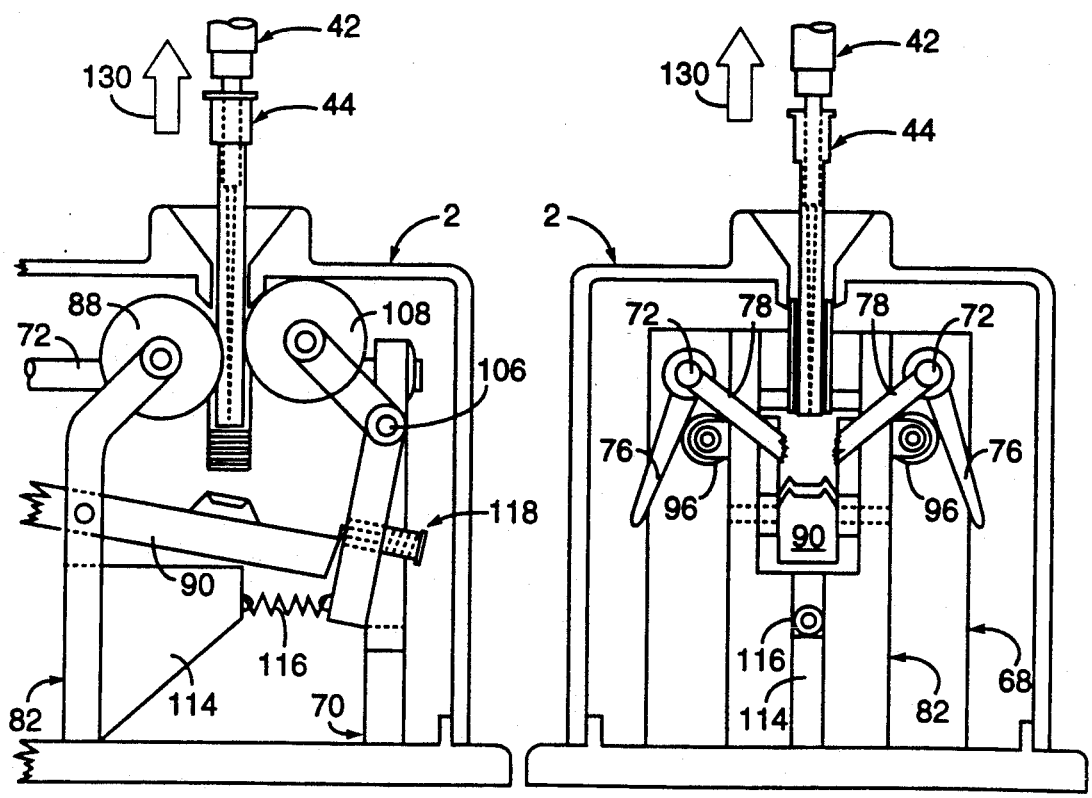

Since the sheath 44 is free from the grip of the jaw members 78 when the lever 90 is latched, the resheathed syringe or catheter 42 may be withdrawn from apparatus by lifting the syringe or catheter in the direction of arrow 130 (FIGS. 20 and 20A). During this withdrawal of the resheathed syringe or catheter, however, the restoring force in spring 116 continues to exert force against the lower portion of yoke member 104 such that the frictionless pulleys remain in rolling contact with the wall of sheath 44 but do not inhibit withdrawal of the syringe or catheter 42 from apparatus 2.

Figures 21, 21A:
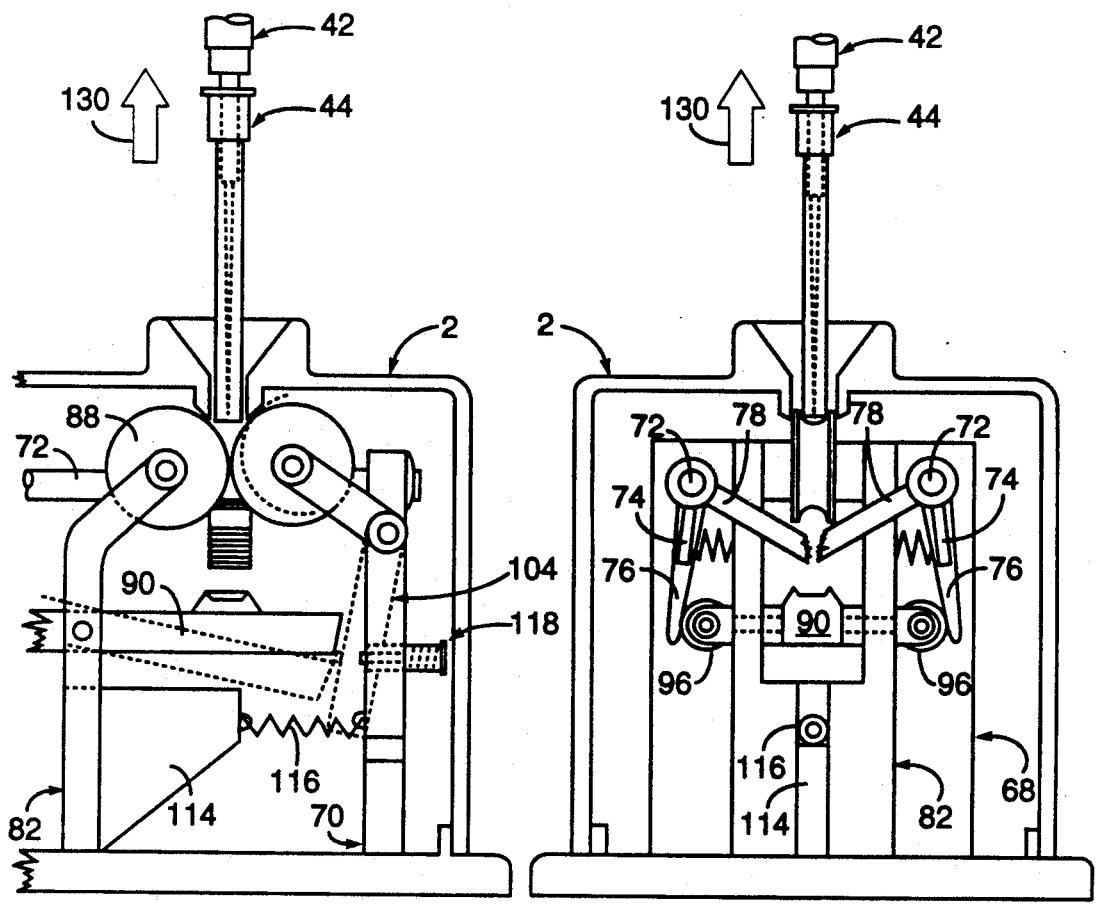

FIGS. 21 and 21A reveal that lifting of the syringe or catheter 42 in the direction of arrow 130 enables the tip 46 of the sheath 44 to clear the pulleys 88 and 108 whereupon spring 116 kicks the lower portion of yoke member 104 away from abutment 114, the end face of the second end of the lever 90 then clears the outwardly protruding latch member 122, and lever 90 and pulley 108 assume their initial positions. In this state, all elements of the second preferred embodiment are returned to their "ready" positions through the combined effects of springs 80 and 116, and to a lesser extent, spring 100.

Figure 22:
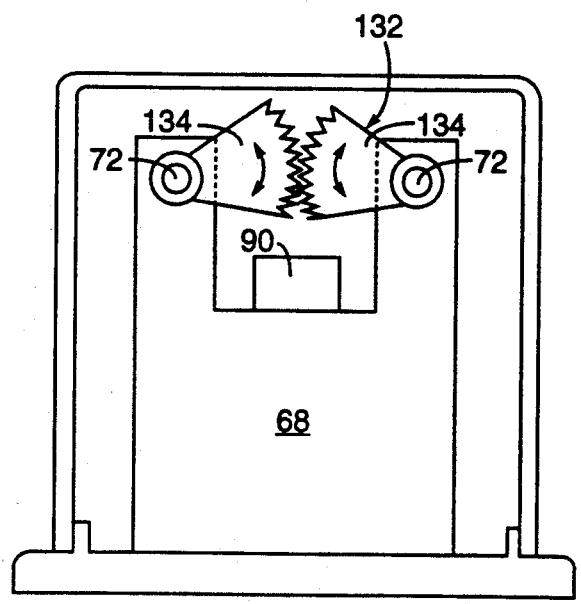
FIG. 22 is a view of a modification of the second embodiment of the medical needle sheath holding apparatus of the present invention.

Turning to FIG. 22 there is shown an optional means 132 for assuring equal and opposite angular displacement of shafts 72 and jaw members 78 upon insertion of syringe or catheter 42 into the second preferred embodiment of medical needle sheath holding apparatus 2 of the present invention. Means 132 consists of a pair of meshing gear sections 134 preferably fixedly mounted to distal ends of shafts 72 at the "left" side of the first upstanding support member 68, as condidered with reference to FIG. 14. As the reader will appreciate, upon insertion into and removal of the syringe or catheter 42 from apparatus 2, the meshing gear sections 134 will assure that the angular displacement of one of the shafts 72 and all elements affixed thereto is at all times equal and opposite to the angular displacement of the other of the shafts 72 and all corresponding counterpart elements affixed thereto.

FIGS. 23, 24, 24A and 24B reveal the operational components of a third preferred embodiment of the present invention. According to this embodiment, which contains many elements similar or identical to those shown in the second preferred embodiment, the medical needle sheath holding apparatus 2 is again unpowered. It is entirely mechanical in operation and does not rely upon electrical power, vacuum, hydraulic pressure, pneumatic pressure, or the like, for motive force or operating power.

Figure 23:
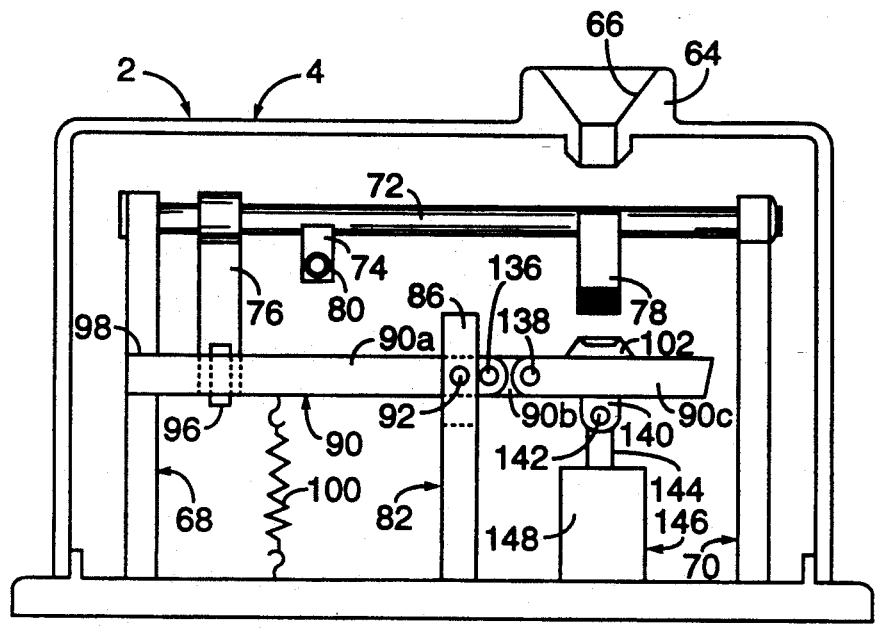
FIG. 23 is a side view of a third embodiment of the medical needle sheath holding apparatus of the present invention with a sidewall and other elements thereof omitted for purposes of clarity.

As is perhaps most clearly seen in FIG. 23, this particular embodiment also includes an elongated generally horizontally extending lever 90 which is pivotally mounted at 92 to arms 84 and 86 of the third upstanding support member 82. Lever 90 according to the third preferred embodiment, however, is preferably jointed at pivot points 136 and 138 and includes first, second and third sections 90a, 90b, and 90c, respectively. The pivotal connections provided by pivots 136 and 138 assure that section 90c remains substantially horizontal during operation, whereby the sheath 44 cannot become misaligned or disengaged from striker plate 102.

Figures 24, 24A:
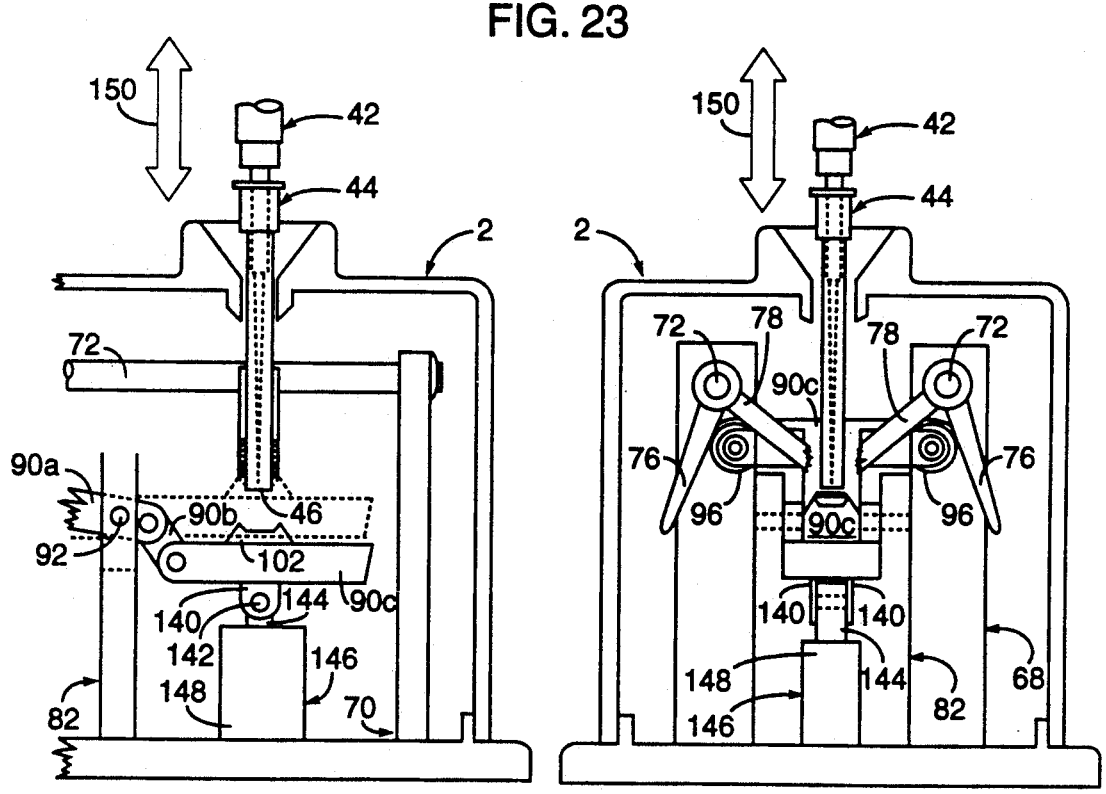
FIGS. 24, 24A and 24B illustrate a typical sequential operation of the third embodiment of the medical needle sheath holding apparatus of the present invention.
Figure 24B:
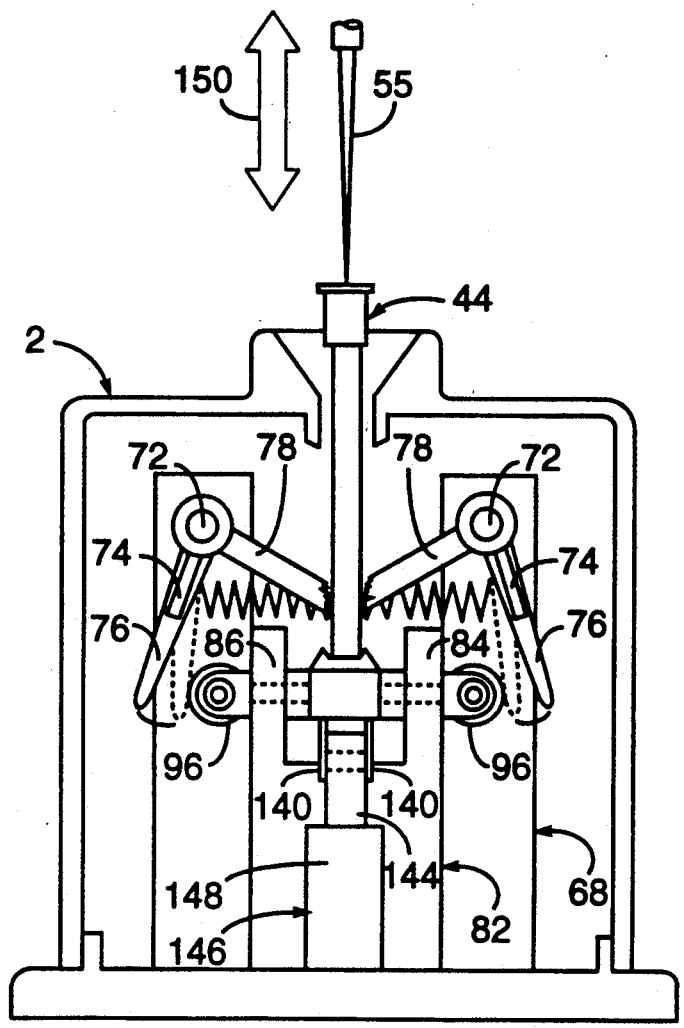

Attached to the bottom of section 90c is a yoke member 140 that is pivotally connected at pivot point 142 to a vertically reciprocable piston portion 144 of a two-position actuator means 146. The piston portion 144 is supported for reciprocation in a cylinder portion 148 of actuator means 146 that is affixed to the base 6 of housing 4. Two-position actuator means 146 possesses an internal two-position latch mechanism and a compression spring which biases piston portion 144 in an upward direction away from base 6. When piston portion 144 is in the upper of its two possible positions, all three sections 90a, 90b, and 90c of lever 90 extend essentially horizontally and jaw members 78 assume their operative or sheath-gripping positions (FIG. 24B).

As will be appreciated from the following, two-position actuator means 146 operates somewhat analogously to the actuating mechanism of a conventional extendable and retractable, two-position, "click" type ball point writing pen. Reference to FIGS. 24, 24A and 24B will reveal the sequence of operations of the third preferred embodiment of the medical needle sheath holding apparatus 2 of the present invention.

Unlike the second preferred embodiment, the operation of the third preferred embodiment of the medical needle sheath holding apparatus 2 begins with the jaw members 78 pivoted outwardly to their non-gripping positions as shown in FIG. 24A. To achieve this situation, the piston portion 144 of two-position actuator means 146 must be situated in the lower of its two positions.

FIGS. 24 and 24A reveal that when piston portion 144 is so positioned, section 90c of lever 90 is also depressed by virtue of its connection to piston portion 144 by yoke member 140 and pivot 142. The distance which section 90c is depressed is sufficient to pivot section 90b downwardly and pull a first end of section 90a downwardly, thereby causing section 90a to pivot about 92. Accordingly, the opposite end of section 90a is pivoted upwardly whereby runner displacement members 94 and the caster wheels 96 drive their respective runner members 76 outwardly, hence pivoting the shafts 72 and the jaw members 78 outwardly into the non-gripping position.

With the jaw members 78 in this position, a sheathed syringe or catheter 42 may then be inserted in the downward direction of double arrow 150 shown in FIGS. 24 and 24A. The sheathed syringe or catheter 42 is inserted until the tip 46 of sheath 44 contacts striker plate 102 whereupon additional downwardly exerted force unlatches the actuator means 146 from its lower position. The unlatching of the actuator means 146 is accompanied by an audible "click" which indicates to the operator that the actuator means is unlatched. The operator then simply withdraws the syringe or catheter from the apparatus 2 in the upward direction of double arrow 150. Simultaneously, the internal spring of the actuator means 146 forces the piston portion 144 and section 90c of lever 90 upwardly, with assistance from the restoring force in tension springs 80 and 100, until the jaw members 78 come into positive gripping engagement with the wall of sheath 44 as shown in FIG. 24B. Once the sheath is gripped, which occurs virtually instantaneously, the syringe or catheter is simply withdrawn from the apparatus 2 whereupon the needle 55 is freed from the sheath and can be used for its intended purpose.

In order to resheath the needle 55, the syringe or catheter is reinserted into the captured sheath in the downward direction of double arrow 150. Downward force is continued until the syringe or catheter is snapped firmly into the sheath and until the piston portion 144 is latched into its lower position, thereby releasing the jaw members from gripping engagement with the walls of the sheath 44 in the manner described hereabove. With the jaw members latched into their non-gripping positions the resheathed needle or catheter may then by withdrawn from apparatus 2.

Figure 25:
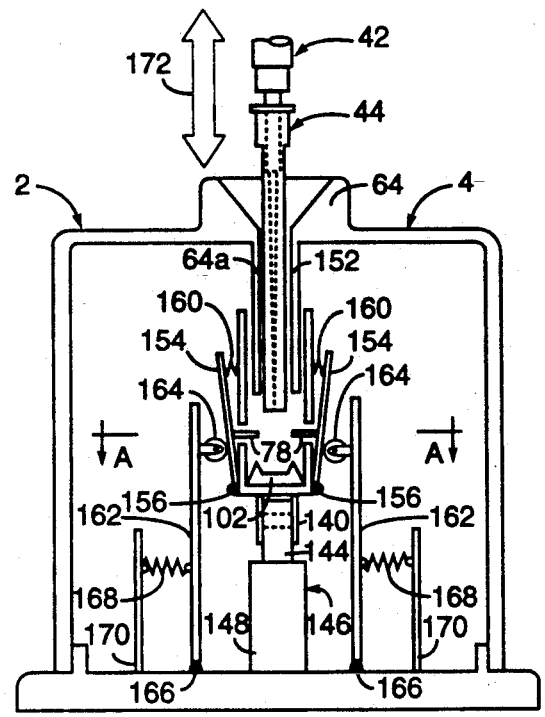
FIGS. 25 and 25A illustrate a typical sequential operation of a fourth embodiment of the medical needle sheath holding apparatus of the present invention.
Figure 25A:
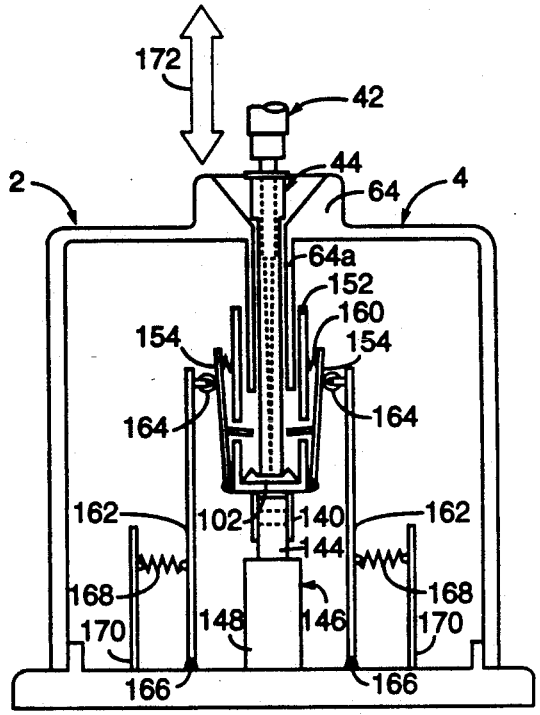

Turning to FIGS. 25 and 25A, there is depicted a fourth preferred embodiment of the medical needle sheath holding apparatus 2 of the present invention. Like the second and third embodiments described hereinabove the fourth embodiment is also unpowered, i.e., it is entirely mechanical in operation. According to this particular embodiment, the raised guide member 64 at the opening to the housing is provided with an elongated downwardly depending annular portion 64a which not only enhances guidance of the syringe or catheter 42 as it is inserted into apparatus 2 but also as a guide for a tubular member 152, the function of which will be described hereinafter.

Like the third embodiment of the present invention, this embodiment also includes a two-position actuator means 146 which is constructed and operates essentially the same as its counterpart previously described with regard to the third embodiment. Piston portion 144 of actuator means 146 may be connected to the bottom of tubular member 152 via yoke member 140 or, alternatively, it may be affixed directly to the bottom of the tubular member. A plurality of runner members 154 are fastened to the exterior of tubular member 152 near the bottom thereof. Preferably the runner members 154 are pivotally fastened to the tubular member as shown at 156, however, it is also contemplated that the runner members can be affixed to the tubular member 152 but be formed of a substantially rigid yet flexible material which will permit flexure of the free ends of the runner members toward and away from the exterior wall of the tubular member 152. If the runner members 154 are pivotally mounted to the tubular member, the free upper ends of runner members 154 are biased outwardly away from the exterior of the tubular member 152 by suitable resilient means 158 such as, for example, compression springs.

Each runner member 154 carries an inwardly directed jaw member 78. The jaw members 78 project through slots or similar openings 160 provided in tubular member 152 such that the gripping edges of the jaw members 78 lie in general opposition to one another in the tubular member.

For each runner member 154, there is provided an upstanding runner displacement member 162, the lower end of which is preferably fastened to the base 6 of housing 4 and the upper end of which rotatably supports a caster wheel 164. It is preferred that the runner displacement members 162 be pivotally fastened to the base 6 as shown at 166. However, it is also possible for the runner displacement members to be affixed to the base 6 but be formed of a substantially rigid yet flexible material which will permit flexure of the upper ends of the runner displacement members whereby the caster wheels 164 will at all times be maintained in rolling contact with the runner members 154. If the runner displacement members are pivotally mounted to base 6, then they must be biased inwardly toward the runner members by resilient means 168, which may suitably take the form of compression springs, or the like, that are held in compression by abutment members 170 secured to housing 4.

The operation of the fourth embodiment of the medical needle sheath holding apparatus of the present invention will be appreciated from combined reference to FIGS. 25 and 25A. According to this particular embodiment, the apparatus 2 is positioned to receive a sheathed syringe or catheter 42 when the piston portion 144 of two-position actuator means 146 is in its upper position (FIG. 25). The sheathed syringe or catheter 42 is then inserted into the apparatus in the downward direction of double arrow 172 until the tip of sheath 44 contacts striker plate 102 whereupon the operator continues to exert downward force against the internal compression spring of actuator means 146 unitl the piston portion 144 of the actuator means is latched into its lower position (FIG. 25A). During the time in which the piston portion 144 is moved from its upper to its lower latched positions, the tubular member 152 and runner members 154 are lowered and caster wheels 164 are caused to roll relatively upwardly along the downwardly traveling runner members 154, thereby pushing the runner members inwardly toward one another until the jaw members 78 grip the sides of the sheath 44. Once the piston portion 144 is latched into the lower position, the jaw members firmly grip the sheath.

With the sheath 44, so gripped, the syringe or catheter 42 can be withdrawn from the sheath by pulling the syringe or catheter in the upward direction of arrow 122 whereby the syringe or catheter may be used for its intended purpose. Still referring to FIG. 25A, when it is desired to resheath the needle of the syringe or catheter 42, the needle is reinserted into the sheath and downward force is applied until the audible "click" of the actuator means is heard indicating the actuator means is unlatched. The operator then withdraws resheathed syringe or catheter from the apparatus 2 in the upward direction of arrow 122. Simultaneously, the internal spring of the actuator means 146 forces the piston portion 144, tubular member 152 and runner members 154 upwardly until the jaw members 78 release from gripping engagement with the sheath. Once released, the resheathed syringe or catheter can be removed from the apparatus 2 whereupon the apparatus returns to its initial position shown in FIG. 25.

Figure 26:
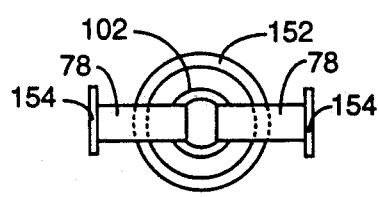
FIG. 26 is a view taken along line A—A of FIG. 25.
Figure 27:
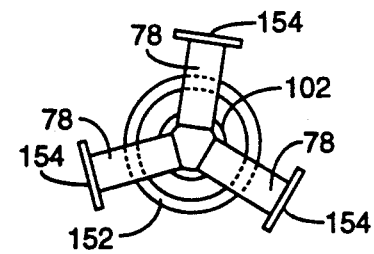
FIG. 27 is a view similar to FIG. 26 depicting a further embodiment of a needle sheath gripping means structure for use with the fourth embodiment of the medical needle sheath holding apparatus of the present invention.

FIGS. 26 and 27 reveal two preferred arrangements of the gripping means for use in the fourth embodiment of the present invention. Although an arrangement including two jaw members 78 as shown in FIG. 26 would be perfectly acceptable, it would be most preferable to have three equiangularly spaced jaw members 78, as seen in FIG. 27, since such an arrangement would effectively prevent lateral shifting of the sheath 44 and thus assure that the sheath remains positively gripped by the jaw members 78 when the jaw members are in their gripping positions.

Figure 28:
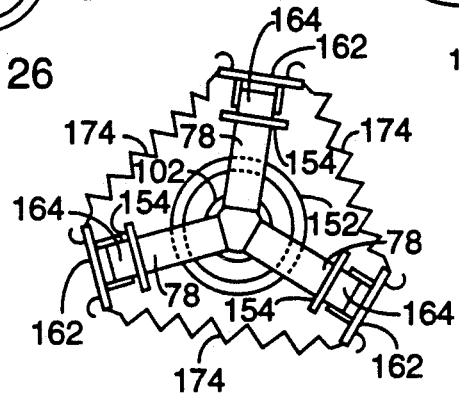
FIG. 28 is a plan view of a modification of the fourth embodiment of the medical needle sheath holding apparatus of the present invention.

FIG. 28 illustrates an alternative to the resilient means 168 and abutment members 170 shown in FIGS. 25 and 25A. According to FIG. 28, the runner displacement members 162 can be joined by yieldable resilient means 174 such as, for example, tension springs having sufficient biasing force to at all times maintain caster sheels 164 in rolling contact with runner members 154. Regardless of whether resilient members 174 or resilient members 168 are used, they must be sufficiently yieldable to accomodate all sizes of medical needle sheaths.

From the foregoing, one skilled in the art will appreciate that the medical needle wheath holder apparatus of the present invention permits an individual to safely and positively unsheath and resheath hypodermic syringe needles, catheter needles, or the like, by using only one hand thus permitting the individual to use his or her free hand for other important activities.

While the present invention has been described in accordance with the preferred embodiments of the various figures, it is to be understood that other similar embodiments may be used or modifications and additions may be made to the described embodiment for performing the same functions of the present invention without deviating therefrom. Therefore, the present invention should not be limited to any single embodiment but rather construed in breadth and scope in accordance with the recitation of the appended claims.

I claim:

1. Apparatus for holding a sheath during unsheathing and resheathing of a needle or catheter, said apparatus permitting a user to perform said unsheathing and resheathing using one hand in a convenient linear stroke-like motion, said apparatus comprising:

means for gripping said sheath, said gripping means being positionable to an operative sheath-gripping position and an inoperative non-gripping position; and entirely mechanical means responsive to insertion of said needle or catheter into said gripping means for positioning said gripping means into said operative and inoperative positions.

2. The apparatus of claim 1 wherein said gripping means comprise jaw members.

3. The apparatus of claim 2 wherein said entirely mechanical means further comprise a latch member and a pivotable lever adapted for displacement by a sheathed needle or catheter, wherein a first end of said lever includes means for moving said jaw members between said operative and inoperative positions and a second end of said lever is releasably engageable by said latch member, said latch member controlling movement of said lever and thereby movement of said jaw members between said operative and inoperative positions.

4. The apparatus of claim 1 further comprising:
   a base;
   first and second upstanding support members secured to said base;
   a pair of substantially parallel shafts supported for rotation in said first and second support members;
   a third upstanding support member secured to said base between said first and second upstanding support members, said third upstanding support member rotatably supporting a first substantially frictionless pulley;
   a yoke member pivotably attached to said second upstanding support member, said yoke member rotatably supporting a second substantially frictionless pulley at a location adjacent said first frictionless pulley;
   said entirely mechanical means comprising a latch member carried by said yoke member and a lever pivotably supported by said third upstanding support member, said lever being adapted for displacement by said needle or catheter,
   wherein, near a first end of said lever, said lever includes means for moving said gripping means between said operative and inoperative positions and a second end of said lever is releasably engageble by said latch number, said latch member controlling movement of said lever and thereby movement of said gripping means between said operative and inoperative positions.

5. The apparatus of claim 4 wherein said gripping means comprise angularly displaceable jaw members affixed to said shafts.

6. The apparatus of claim 5 further comprising force transmitting members affixed to said shafts, said force transmitting members being adapted for contact by said means for moving said gripping means so as to convert pivotable movement of said lever into angular movement of said shafts and said jaw members.

7. The apparatus of claim 6 wherein said entirely mechanical means further comprise means for biasing said jaw members into a ready position adapted to receive a sheathed needle or catheter.

8. The apparatus of claim 7 wherein said biasing means comprise first resilient means for drawing said force transmitting members toward one another under tension.

9. The apparatus of claim 8 further comprising second resilient means for biasing said yoke member such that said second pulley is continually biased in a direction toward said first pulley.

10. The apparatus of claim 9 further comprising third resilient means for biasing said first end of said lever toward said base.

11. The apparatus of claim 4 further comprising means for biasing said latch member toward said second end of said lever.

12. The apparatus of claim 4 further comprising means for ensuring equal and opposite angular displacement of said shafts upon insertion of a needle or catheter into said gripping means.

13. The apparatus of claim 1 further comprising:
a base;
first and second upstanding support members secured to said base;
a pair of substantially parallel shafts supported for rotation in said first and second support members;
a third upstanding support member secured to said base between said first and second upstanding support members;
said entirely mechanical means comprising a two-position actuator means carried by said base and a lever pivotably supported by said third upstanding support member, said lever being adapted for displacement by said needle or catheter,
wherein, near a first end of said lever, said lever includes means for moving said gripping means between said operative and inoperative positions and, near a second end of said lever, said lever is connected to said actuator means, said actuator means being operative in a first position thereof to cause said gripping means to assume said operative position and in a second position thereof to cause said gripping means to assume said inoperative position.

14. The apparatus of claim 13 wherein said gripping means comprise angularly displaceable jaw members affixed to said shafts.

15. The apparatus of claim 14 further comprising force transmitting members affixed to said shafts, said force transmitting members being adapted for contact by said means for moving said gripping means so as to convert pivotable movement of said lever into angular movement of said shafts and said jaw members.

16. The apparatus of claim 15 further comprising first resilient means for drawing said force transmitting members toward one another under tension.

17. The apparatus of claim 16 further comprising second resilient means for biasing said first end of said lever toward said base.

18. The apparatus of claim 1 wherein said entirely mechanical means comprise a two-position actuator means, said actuator means being operative in a first position thereof to cause said gripping means to assume said operative position and in a second position thereof to cause said gripping means to assume said inoperative position.

19. The apparatus of claim 18 wherein said gripping means comprise jaw members.

20. The apparatus of claim 19 further comprising means for operably connecting said jaw members to said actuator means, said means for operably connecting being adapted for displacement by said needle or catheter in order to position said actuator means into said first position thereof and into said second position thereof.

21. The apparatus of claim 20 further comprising means for urging said jaw members into said operative position upon positioning of said actuator means into said first position thereof, said means for urging enabling said jaw members to move into said inoperative position upon positioning of said actuator means into said second position thereof.

22. Apparatus for holding a sheath during unsheathing and resheathing of a needle or catheter, said apparatus permitting a user to perform said unsheathing and resheathing using one hand in a convenient linear stroke-like motion, said apparatus comprising:
means for gripping said sheath, said gripping means being positionable to an operative sheath-gripping position and an inoperative non-gripping position; and
means responsive to insertion of said needle or catheter into said gripping means for positioning said gripping means into said operative and inoperative positions.

* * * * *